(12) United States Patent
Hatanaka et al.

(10) Patent No.: US 9,390,549 B2
(45) Date of Patent: Jul. 12, 2016

(54) SHAPE DATA GENERATION METHOD AND APPARATUS

(71) Applicants: FUJITSU LIMITED, Kawasaki-shi, Kanagawa (JP); The University of Tokyo, Tokyo (JP)

(72) Inventors: Kohei Hatanaka, Fujisawa (JP); Toshiaki Hisada, Tokyo (JP); Seiryo Sugiura, Tokyo (JP); Takumi Washio, Tokyo (JP); Jun-ichi Okada, Tokyo (JP)

(73) Assignees: FUJITSU LIMITED, Kawasaki (JP); The University of Tokyo, Tokyo (JP)

( * ) Notice: Subject to any disclaimer, the term of this patent is extended or adjusted under 35 U.S.C. 154(b) by 0 days.

(21) Appl. No.: 14/629,541

(22) Filed: Feb. 24, 2015

(65) Prior Publication Data

US 2015/0199840 A1 Jul. 16, 2015

Related U.S. Application Data

(63) Continuation of application No. PCT/JP2012/071502, filed on Aug. 24, 2012.

(51) Int. Cl.
*G06T 15/08* (2011.01)
*A61B 6/00* (2006.01)
(Continued)

(52) U.S. Cl.
CPC .............. *G06T 15/08* (2013.01); *A61B 6/032* (2013.01); *A61B 6/5211* (2013.01);
(Continued)

(58) Field of Classification Search
None
See application file for complete search history.

(56) References Cited

U.S. PATENT DOCUMENTS 6,008,813 A * 12/1999 Lauer .................. G06T 1/60
345/418
6,396,898 B1 * 5/2002 Saito .................. G01N 23/046
378/19

(Continued)

FOREIGN PATENT DOCUMENTS

EP 2 369 553 A2 9/2011
JP H08-191387 A 7/1996

(Continued)

OTHER PUBLICATIONS

International Search Report issued Nov. 27, 2012 for PCT/JP2012/071502 filed on Aug. 24, 2012 with English Translation.

(Continued)

*Primary Examiner* — Said Broome
(74) *Attorney, Agent, or Firm* — Oblon, McClelland, Maier & Neustadt, L.L.P.

(57) ABSTRACT

A shape data generation method relating to this invention includes: first generating first three-dimensional voxel data that represents a target object by using first tomographic images, in which a first region occupied by the target object is designated, among plural tomographic images; extracting, from the first tomographic images, brightness values of voxels included in the first region; second generating a function for calculating a probability that a voxel is included in the first region by using the extracted brightness values; calculating, for each voxel among voxels in a voxel space that includes the plural tomographic images, a probability by using a brightness value of the voxel and the function; and third generating second three-dimensional voxel data that represents the target object by using the first three-dimensional voxel data and probabilities calculated for the voxels in the voxel space.

11 Claims, 24 Drawing Sheets

(51) Int. Cl.
- A61B 6/03 (2006.01)
- G06T 7/00 (2006.01)
- G06T 15/50 (2011.01)

(52) U.S. Cl.
CPC ............ *G06T 7/0012* (2013.01); *G06T 7/0081* (2013.01); *G06T 7/0087* (2013.01); *G06T 7/0089* (2013.01); *G06T 15/50* (2013.01); *A61B 6/466* (2013.01); *A61B 2576/00* (2013.01); *G06T 2207/10072* (2013.01); *G06T 2207/20076* (2013.01); *G06T 2207/20081* (2013.01); *G06T 2207/20104* (2013.01); *G06T 2207/30048* (2013.01)

(56) References Cited

U.S. PATENT DOCUMENTS

| | | | |
|---|---|---|---|
| 7,515,948 B1 * | 4/2009 | Balberg | A61B 5/0095 600/323 |
| 2002/0184470 A1 | 12/2002 | Weese et al. | |
| 2008/0013810 A1 * | 1/2008 | Matsumoto | G06T 11/008 382/128 |
| 2008/0044080 A1 | 2/2008 | Li | |
| 2008/0075346 A1 * | 3/2008 | Matsumoto | G06T 15/08 382/131 |
| 2009/0080745 A1 | 3/2009 | Zheng et al. | |
| 2012/0301053 A1 | 11/2012 | Watanabe et al. | |

FOREIGN PATENT DOCUMENTS

| | | |
|---|---|---|
| JP | 2002-329216 A | 11/2002 |
| JP | 2004-265337 A | 9/2004 |
| JP | 2007-098028 A | 4/2007 |
| JP | 2007-144056 A | 6/2007 |
| JP | 2007-164592 A | 6/2007 |
| JP | 2007-307358 A | 11/2007 |
| JP | 2008-009549 A | 1/2008 |
| JP | 2012-245085 A | 12/2012 |

OTHER PUBLICATIONS

Satake, Koji, et al., "Liver Segmentation Method for 3D Non-contrast Abdominal CT Image based on the Region Growing and the Probabilistic Atlas," *IEICE Technical Report. Image Engineering*, May 15, 2008, vol. 108, No. 45, pp. 81-85, with English Abstract.

Sakamoto, Yoshitaka et al., "Detection of the Liver Hemangioma from 3D Abdominal CT Images by Using Local Intensity Features and Multi-case Classifier," *IEICE Technical Report*, Jan. 19, 2012, vol. 111, No. 389, pp. 383-388, with English Abstract.

Kitagawa, Teruhiko, et al., "Generation of a Probabilistic Liver Atlas and Its Application to Automated Liver Segmentation Method in Non-contrast X-Ray Torso CT Images," *The IEICE Transactions on Information and Systems*, Jul. 1, 2008, vol. J91-D, No. 7, pp. 1837-1850.

Kimoto, Tatsuya et al., "Pancreas Segmentation from Three Dimensional Contrast Enhanced CT Images Based on a Patient Specific Atlas," *IEICE Technical Report*, Jan. 12, 2009, vol. 108, No. 385, pp. 181-186, with English Abstract.

Treameau, Alain, et al., "A Region Growing and Merging Algorithm to Color Segmentation," *Pattern Recognition*, 1997, vol. 30, No. 7, pp. 1191-1203.

Bookstein, Fred L., "Principal Warps: Thin-Plate Splines and the Decomposition of Deformations," *IEEE Transactions on Pattern Analysis and Machine Intelligence*, Jun. 1989, vol. 11, No. 6, pp. 567-585.

Vincent, Luc., "Morphological Grayscale Reconstruction in Image Analysis: Applications and Efficient Algorithms," *IEEE Transactions on Image Processing*, Apr. 1993, vol. 2, No. 2, pp. 176-201.

Sorkine, O., "Laplacian Surface Editing," *SGP 04 Proceedings of the 2004 Eurographics/ACM SIGGRAPH Symposium on Geometry Processing*, 2004, pp. 175-184.

Partial Supplementary European Search Report issued Jul. 16, 2015 in Patent Application No. 12883124.5.

Guillermo Sapiro, et al., "Geometric Approaches for Segmentation and Signal Detection in Functional MRI analysis" Signal Processing for Magnetic Resonance Imaging and Spectroscopy, CRC Press, XP055200045, Feb. 20, 2002, pp. 317-339.

James L. Crowley, "Intelligent Systems: Reasoning and Recognition" Two Views on Bayes Rule, URL:http://www-prima.imag.fr/jlc/Courses/2009/ENSI2.SIRR/ENSI2.SIRR.S13.pdf, XP055200047, Mar. 31, 2010, 11 Pages.

Marcel Prastawa, et al., "A brain tumor segmentation framework based on outlier detection" Medical Image Analysis, XP004533586, vol. 8, No. 3, Sep. 2004, pp. 275-283.

Huseyin Tek, et al., "Image Segmentation by Reaction-Diffusion Bubbles" Computer Vision, Fifth International Conference on Cambridge, MA, XP010147023, Jun. 20, 1995, pp. 156-162.

Extended European Search Report issued on Jan. 15, 2016 in the corresponding European Application No. 12883124.5.

\* cited by examiner

| NO. | VALUE |
|---|---|
| 0x0000 | 0.456 |
| | 0.5 |
| ⋮ | ⋮ |
FIG.7
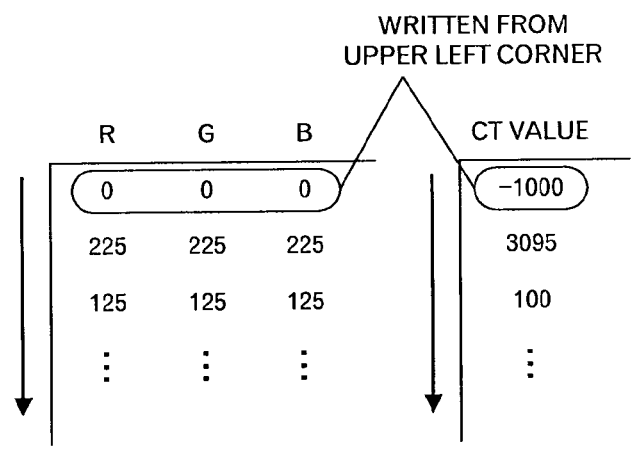
FIG.8
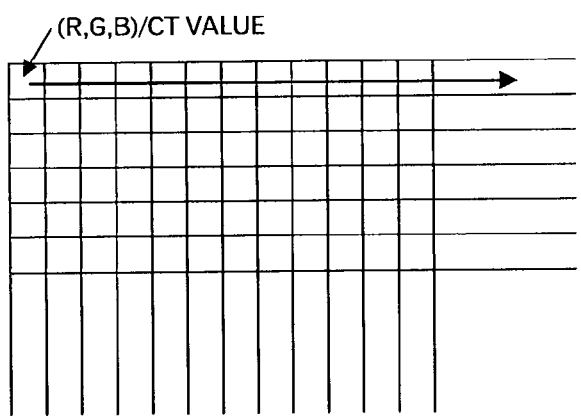
FIG.9

| INNER REGION | | OUTER REGION | |
|---|---|---|---|
| (i, j, k) | I(i, j, k) | (i, j, k) | I(i, j, k) |
| (,,) | 377 | (,,) | 14 |
| (,,) | 210 | (,,) | 73 |
| (,,) | 258 | (,,) | 51 |
| ⋮ | ⋮ | ⋮ | ⋮ |

# SHAPE DATA GENERATION METHOD AND APPARATUS

CROSS-REFERENCE TO RELATED APPLICATIONS

This application is a continuing application, filed under 35 U.S.C. section 111(a), of International Application PCT/JP2012/071502, filed on Aug. 24, 2012, the entire contents of which are incorporated herein by reference.

FIELD

This invention relates to a shape data generation method and a shape data generation apparatus.

BACKGROUND

In the medical field, simulators, such as an operation simulator and an organ simulator, are used for determination of a treatment policy, diagnosis, postoperative prediction, development of pharmaceuticals and medical equipment, or the like. In the simulation by such simulators, three-dimensional shape data of organs is used, but it is often not easy to generate the three-dimensional shape data of organs. The reasons are that organs are not visible, and are not directly measurable since they exist in the inside of a living body, and also that the shapes of organs are complicated originally.

Conventionally, there is a technique to generate the three-dimensional shape data used for a simulation by extracting a target region based on brightness values of tomographic images (for example, a Region Growing method) such as CT (Computed Tomography) images and MRI (Magnetic Resonance Imaging) images. For example, assume that a region surrounded by a solid line 21 (a region of the right ventricular fluid) and a region surrounded by a solid line 22 (a region of the left ventricular fluid) in FIG. 2 are to be extracted from tomographic image data of a heart illustrated in FIG. 1 by the Region Growing method, and that the three-dimensional shape data of the right ventricular fluid and the left ventricular fluid are to be generated. However, when the Region Growing method is carried out actually to the tomographic image data of the heart illustrated in FIG. 1, a result illustrated in FIG. 3 is obtained. As illustrated in FIG. 3, a portion of the region of the right ventricular fluid cannot be extracted due to influence of a contrast medium. Moreover, a region corresponding to a papillary muscle in the left ventricular fluid cannot be extracted too. Thus, there is a limit to extract the region based only on the brightness values.

Moreover, there is a technique to find an evaluation function for estimating, based on its feature quantity, whether or not a pixel is a pixel which represents an outline to calculate an evaluation value which represents whether a pixel in the region is a pixel on the outline by using the evaluation function, and to determine the outline based on the evaluation value.

Moreover, there is a technique to minimize crushing of a small edge in an image binarized by an error diffusion method and convert to a clear gray-scale image with high tone. Specifically, at least the edge strength of a target pixel in an inputted binary image is detected, and a threshold of the brightness of the image is set based on the detection result. The size of a multi-level filter is determined by comparing a percentage of black pixels and white pixels in the plural multi-level filters with the threshold. Then, the binary image data is converted to gray-scale image data based on the percentage of the black pixels and white pixels in the multi-level filter with the determined size.

However, it is not possible to generate the three-dimensional shape data with high precision by using techniques as described above because there is a case where a target region can't be extracted accurately.

Patent Document 1: Japanese Laid-open Patent Publication No. 2007-307358

Patent Document 2: Japanese Laid-open Patent Publication No. 08-191387

Non-Patent Document 1: A. Tremeau, N. Borel, "A Region Growing and Merging Algorithm to Color Segmentation", Pattern recognition, Volume 30, Issue 7, July 1997, Pages 1191-1203

SUMMARY

A shape data generation method relating to this invention includes: first generating first three-dimensional voxel data that represents a target object by using first tomographic images, in which a first region occupied by the target object is designated, among plural tomographic images; extracting, from the first tomographic images, brightness values of voxels included in the first region; second generating a function for calculating a probability that a voxel is included in the first region by using the extracted brightness values; calculating, for each voxel among voxels in a voxel space that includes the plural tomographic images, a probability by using a brightness value of the voxel and the function; and third generating second three-dimensional voxel data that represents the target object by using the first three-dimensional voxel data and probabilities calculated for the voxels in the voxel space.

The object and advantages of the embodiment will be realized and attained by means of the elements and combinations particularly pointed out in the claims.

It is to be understood that both the foregoing general description and the following detailed description are exemplary and explanatory and are not restrictive of the embodiment, as claimed.

BRIEF DESCRIPTION OF DRAWINGS

FIG. 7 is a diagram depicting an example of header information included in DICOM (Digital Imaging and COmmunication in Medicine) data;

FIG. 8 is a diagram depicting an example of brightness value information included in the DICOM data;

FIG. 9 is a diagram to explain a description method of a pixel value;

DESCRIPTION OF EMBODIMENTS

Figure 4:
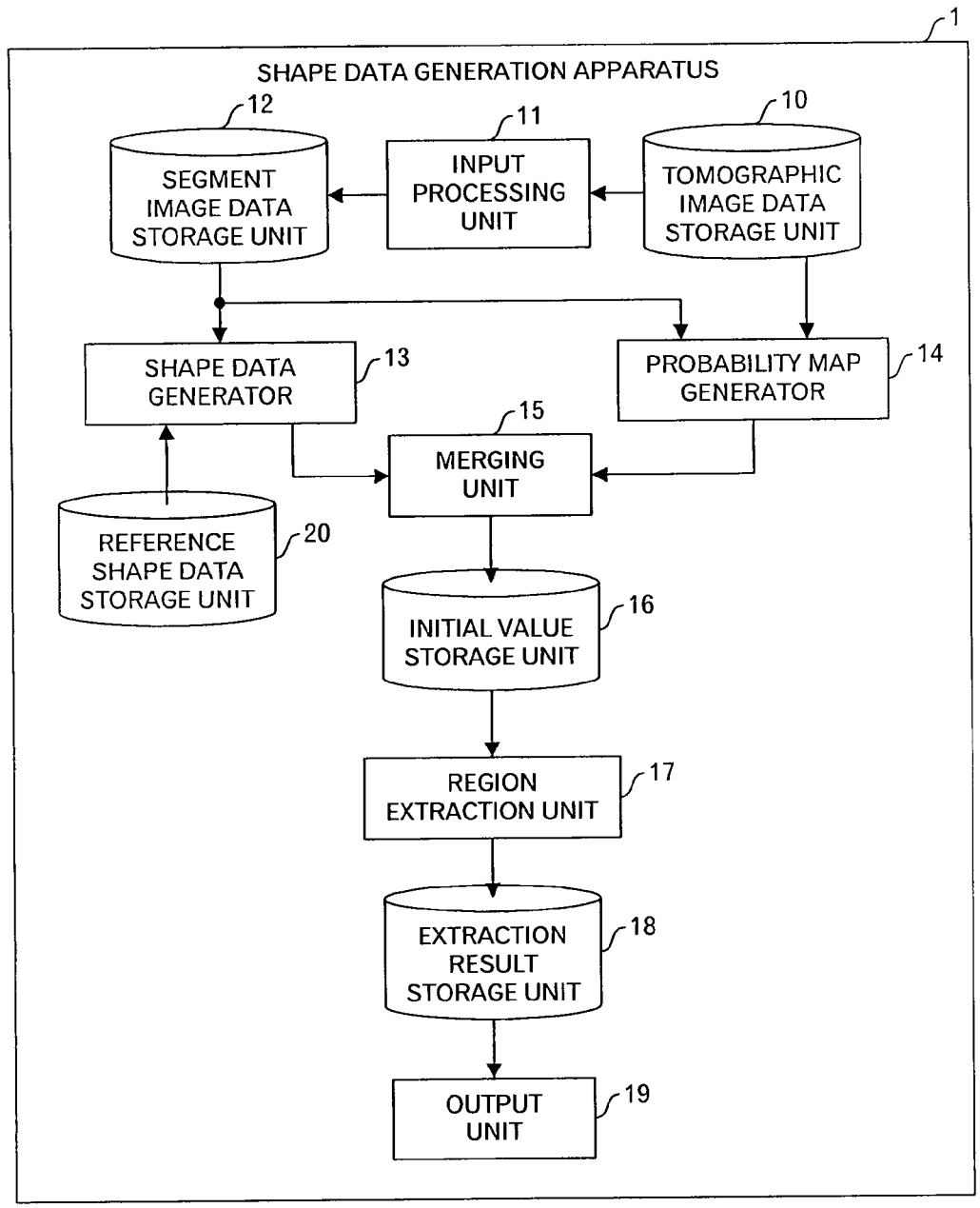
FIG. 4 is a functional block diagram of a shape data generation apparatus.

FIG. 4 illustrates a functional block diagram of a shape data generation apparatus in this embodiment. The shape data generation apparatus 1 includes a tomographic image data storage unit 10, an input processing unit 11, a segment image data storage unit 12, a shape data generator 13, a probability map generator 14, a merging unit 15, an initial value storage unit 16, a region extraction unit 17, an extraction result storage unit 18, an output unit 19, and a reference shape data storage unit 20.

The input processing unit 11 accepts designation of a region, which is used in a simulation, to data of tomographic images stored in the tomographic image data storage unit 10 from the user. Then, the input processing unit 11 stores the tomographic image data, in which the region has been designated (hereinafter referred to as the segment image data), in the segment image data storage unit 12. The shape data generator 13 uses data that is stored in the segment image data storage unit 12 and data that is stored the reference shape data storage unit 20 to perform a shape data generation processing, which will be described later, and generates shape data. The probability map generator 14 uses data that is stored in the segment image data storage unit 12 and data that is stored in the tomographic image data storage unit 10 to perform a probability map generation processing, which will be described later, and generate a probability map. The merging unit 15 generates an initial value by using the shape data generated by the shape data generator 13 and the probability map generated by the probability map generator 14, and stores the initial value in the initial value storage unit 16. The region extraction unit 17 uses initial value that is stored in the initial value storage unit 16 to perform a region extraction processing, and stores the processing result in the extraction result storage unit 18. The output unit 19 displays data stored in the extraction result storage unit 18 on a display device (for example, a monitor).

Figure 5:
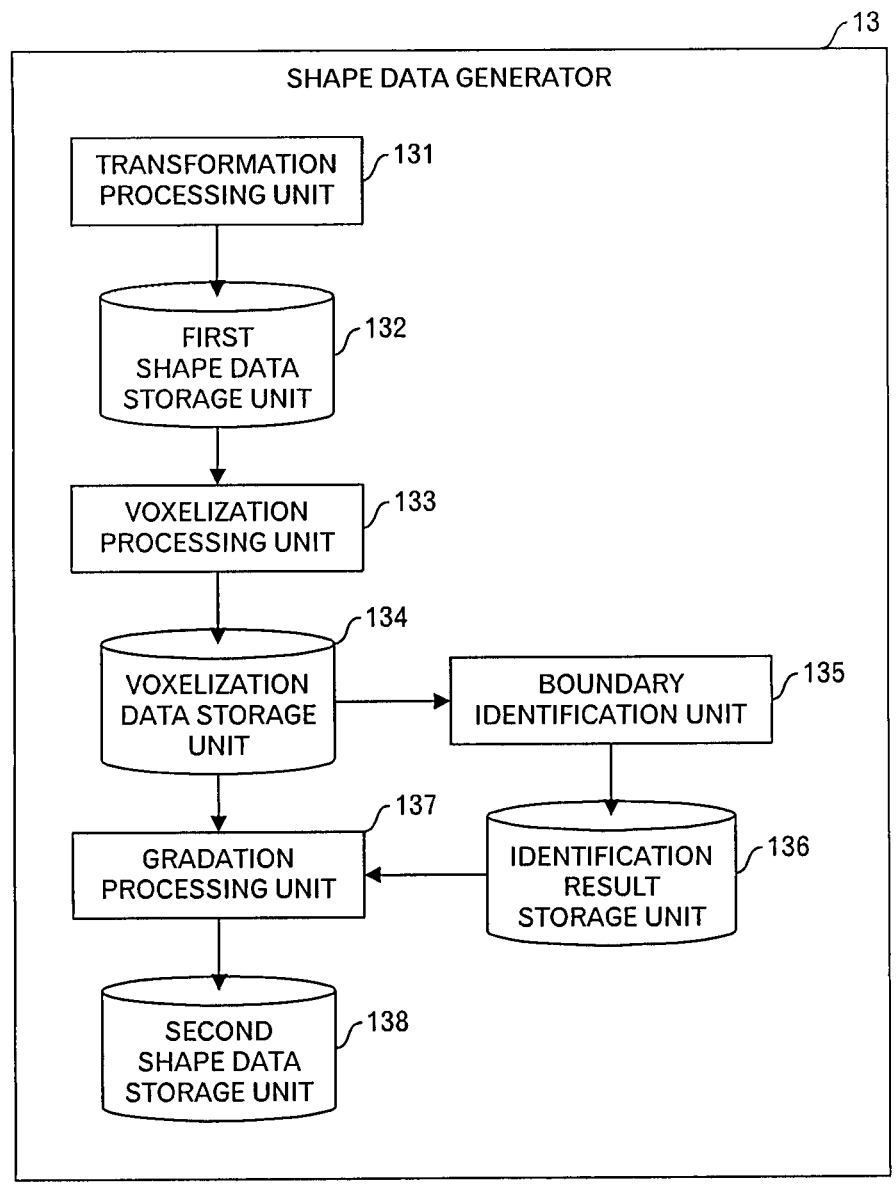
FIG. 5 is a functional block diagram of a shape data generator.

FIG. 5 illustrates a functional block diagram of the shape data generator 13. The shape data generator 13 includes a transformation processing unit 131, a first shape data storage unit 132, a voxelization processing unit 133, a voxelization data storage unit 134, a boundary identification unit 135, an identification result storage unit 136, a gradation processing unit 137, and a second shape data storage unit 138.

The transformation processing unit 131 uses data that is stored in the segment image data storage unit 12 to transform reference shape data (standard shape data of the left ventricular fluid (this includes portions of papillary muscle) in this embodiment) stored in the reference shape data storage unit 20, and stores the transformed shape data in the first shape data storage unit 132. The voxelization processing unit 133 performs a voxelization processing, which will be described later, to shape data stored in the first shape data storage unit 132, and stores the processing result in the voxelization data storage unit 134. The boundary identification unit 135 uses data that is stored in the voxelization data storage unit 134 to perform a processing to identify voxels corresponding to a boundary between the left ventricular fluid and a part which is not the left ventricular fluid, and stores the processing result in the identification result storage unit 136. The gradation processing unit 137 uses data that is stored in the voxelization data storage unit 134 and data that is stored in the identification result storage unit 136 to perform a gradation processing, and stores the processing result in the second shape data storage unit 138.

Figure 6:
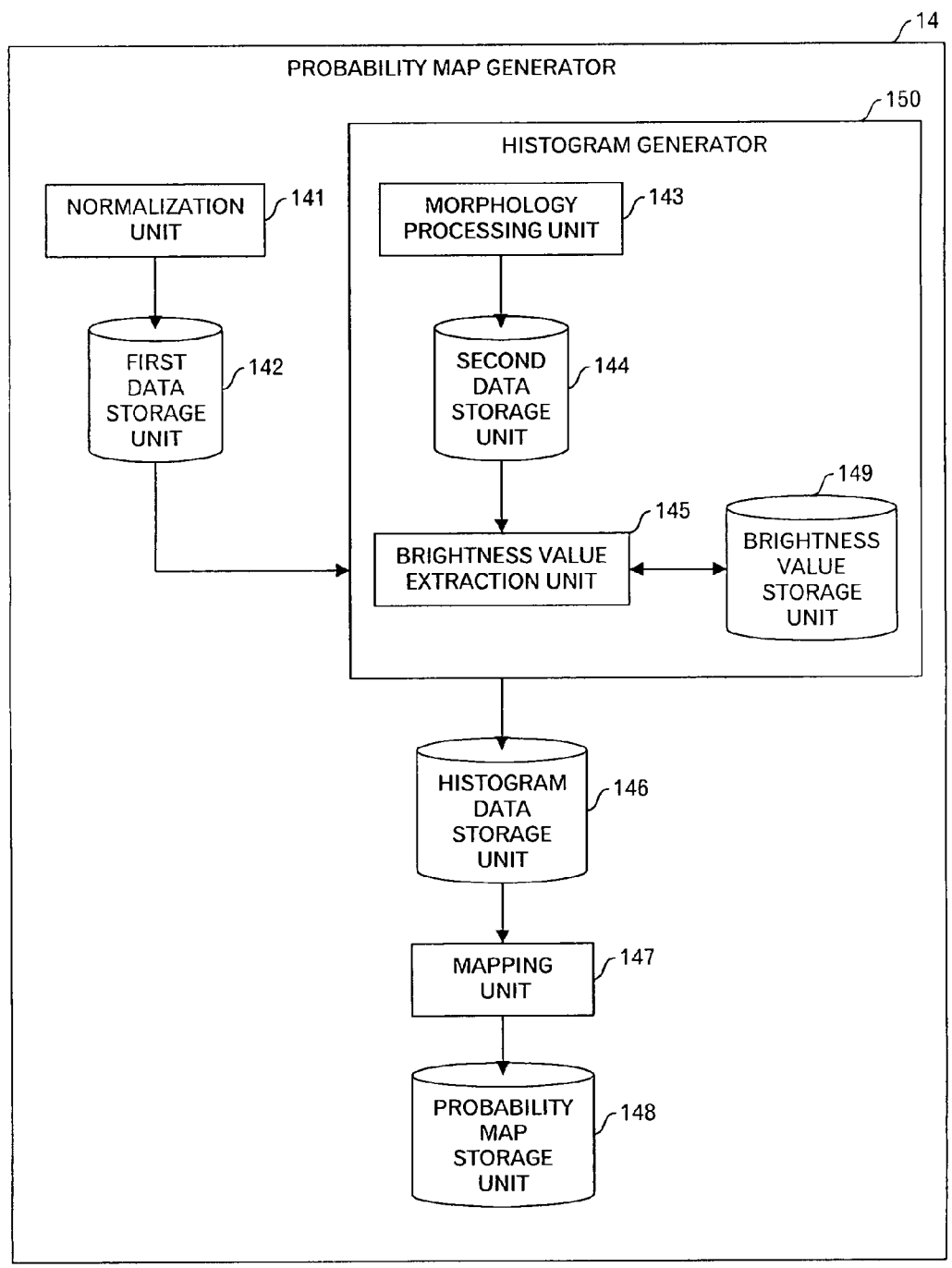
FIG. 6 is a functional block diagram of a probability map generator.

FIG. 6 illustrates a functional block diagram of the probability map generator 14. The probability map generator 14 includes a normalization unit 141, a first data storage unit 142, a histogram generator 150, a histogram data storage unit 146, a mapping unit 147, and a probability map storage unit 148. The histogram generator 150 includes a morphology processing unit 143, a second data storage unit 144, a brightness value extraction unit 145, and a brightness value storage unit 149.

The normalization unit 141 performs a processing to normalize brightness values of tomographic image data stored in the tomographic image data storage unit 10, and stores the processing result in the first data storage unit 142. The morphology processing unit 143 performs an erosion processing to a designated region in the segment image data stored in the segment image data storage unit 12, and stores the processing result in the second data storage unit 144. The brightness value extraction unit 145 uses data that is stored in the first data storage unit 142 and data that is stored in the second data storage unit 144 to perform a processing, and stores the processing result in the brightness value storage unit 149. Moreover, the brightness value extraction unit 145 uses data that is stored in the brightness value storage unit 149 to generate a histogram, and stores the histogram in the histogram data storage unit 146. The mapping unit 147 uses data that is stored in the histogram data storage unit 146 to perform a processing to map probability data to each voxel in a voxel space that includes tomographic image data stored in the tomographic image data storage unit 10, and stores the processing result in the probability map storage unit 148.

Figure 1:
FIG. 1 is a diagram depicting a tomographic image of a heart.
Figure 2:
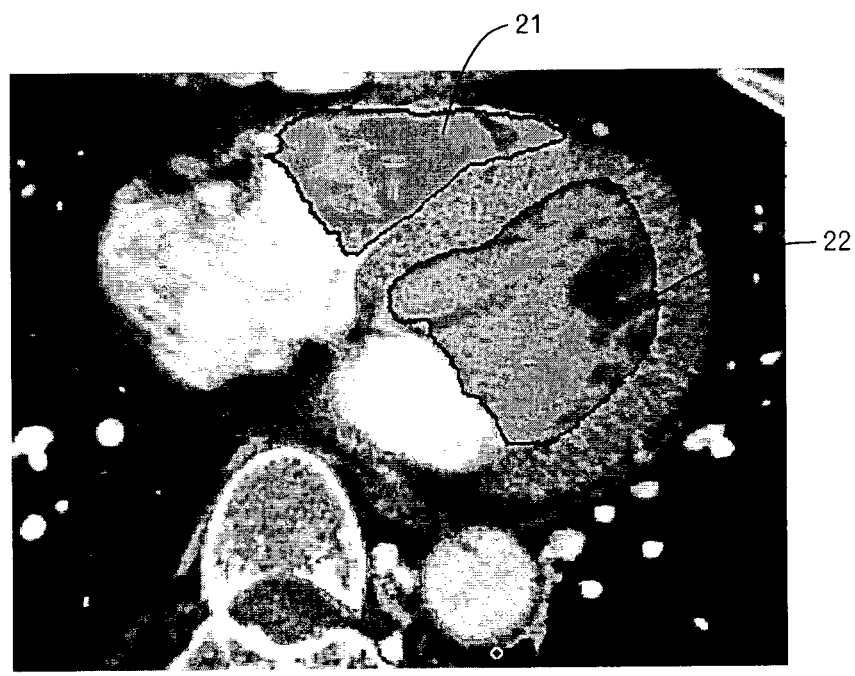
FIG. 2 is a diagram depicting the tomographic image of the heart, which overlaps with a region used in a simulation.
Figure 3:
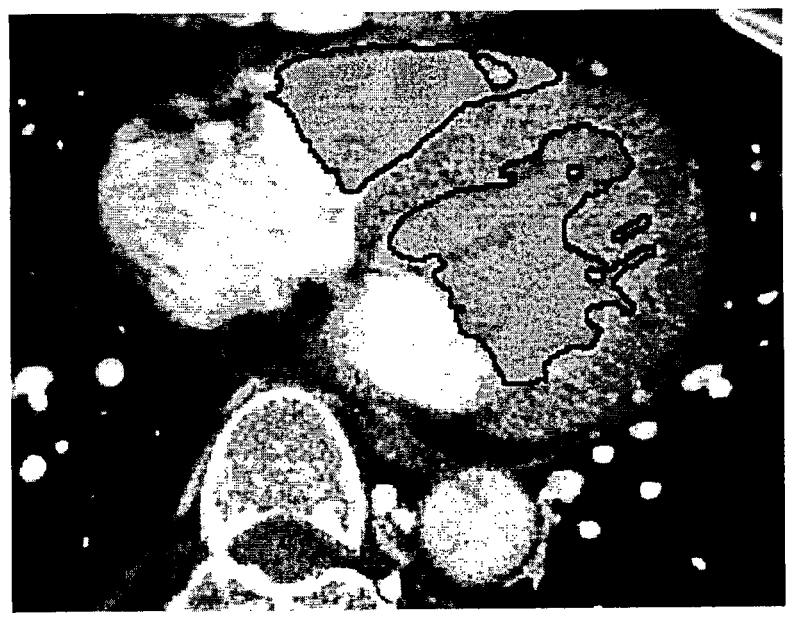
FIG. 3 is a diagram depicting a result of a Region Growing method applied to the tomographic image of the heart.

For example, data of multiple tomographic images as illustrated in FIG. 1 is stored in the tomographic image data storage unit 10. The format of the tomographic image data is, for example, DICOM (Digital Imaging and COmmunication in Medicine). Data in DICOM format includes header information and brightness value information. As illustrated in FIG. 7, the header information includes, for each number, patient information, a type of the medical measurement equipment, information on a resolution of tomographic images, and the like. In FIG. 7, "0.456" represents a width (millimeter) for one pixel, and "0.5" represents a distance (millimeter) between tomographic images. Moreover, as illustrated in FIG. 8, the brightness value information includes values of red (R), green (G), and blue (B). In case of CT, the brightness value information includes the value called CT value (the unit is Hounsfield Unit), the minimum value is −1000, and the maximum value is 3095. As illustrated in FIG. 9, each pixel value in FIG. 8 is written rightward from the upper left corner of a tomographic image, and is written, in a similar fashion, rightward from the left end of the next line when it reaches the right end. Data that includes three-dimensional shape of organs can be generated by laminating multiple tomographic images obtained by CT, MRI, and the like. This data is called volume data.

Figure 10:
FIG. 10 is a diagram depicting an example of data stored in a segment image data storage unit.

FIG. 10 illustrates an example of data stored in the segment image data storage unit 12. An example in FIG. 10 is image data that Predetermined label values are given to a region (a portion of the left ventricular fluid (this includes portions of the papillary muscle) in this embodiment) in tomographic image data illustrated in FIG. 1, which has been designated as a portion used in a simulation by a user. Such segment image data of multiple segment images is stored in the segment image data storage unit 12. A user manually designates a region in a part of tomographic image data stored in the tomographic image data storage unit 10 (for example, 1 sheet for 30 sheets). Designating a region is sometimes called segmentation.

Data for the reference shape of a left ventricular fluid is stored in the reference shape data storage unit 20. More specifically, STL (Standard Triangulated Language) data that contains information about the vertices of the shape and information about connection of vertices is stored, and the shape includes triangular mesh. However, the data format is not limited to the format of the STL data.

Next, the operation of the shape data generation apparatus 1 that is illustrated in FIG. 4 will be explained by using FIGS. 11 to 30.

Figure 11:
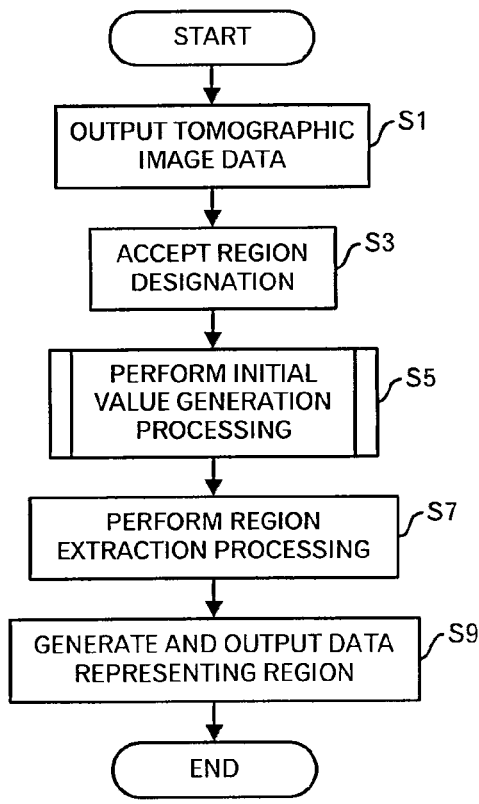
FIG. 11 is a diagram depicting a main processing flow.

First, the input processing unit 11 outputs a part of tomographic image data (for example, 1 sheet per 30 sheets) stored in the tomographic image data storage unit 10 on a display device in order (FIG. 11: step S1). In this way, a user who is a doctor or the like is prompted to designate a region. The user gives, by manipulating a computer mouse or the like, a target region (a region which is the left ventricular fluid in this embodiment) in the tomographic image data a label value. In response to this, the input processing unit 11 accepts designation of the region (step S3), and stores segment image data, which was created by the region designation by the user, in the segment image data storage unit 12.

Then, the shape data generation apparatus 1 performs an initial value generation processing (step S5). The initial value generation processing will be explained by using FIGS. 12A to 26.

Figure 12A:
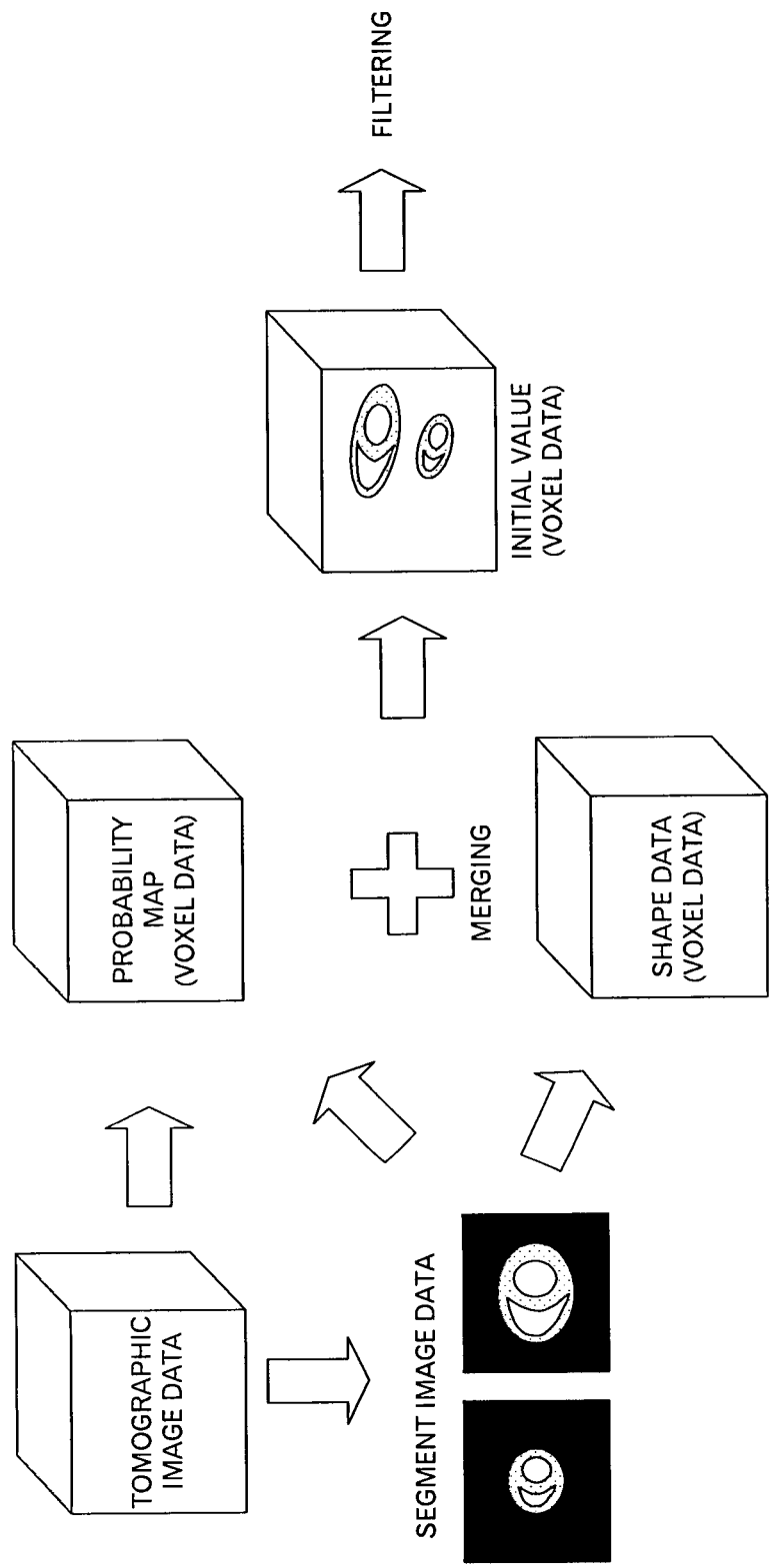
FIG. 12A is a diagram to explain an outline of an initial value generation processing.

First, a summary of the initial value generation processing will be explained by using FIG. 12A. An initial value generated by the initial value generation processing is data in a voxel space, and is used as an initial value of a reaction diffusion filter, which will be described later. The initial value is generated by merging the shape data and the probability map. The shape data is obtained by transforming reference shape data so as to match a shape identified by the segment image data. The probability map is obtained by mapping probability data to each voxel in the tomographic image data by using a histogram of brightness values, which was generated by the segment image data.

A processing flow of the initial value generation processing will be explained in the following.

Figure 12B:
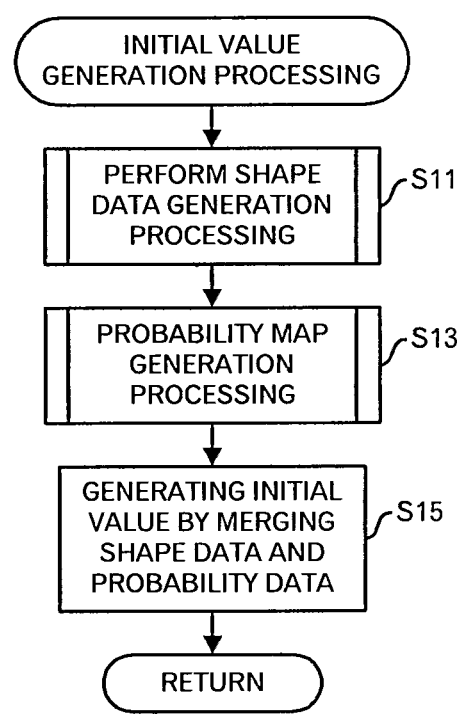
FIG. 12B is a diagram depicting a processing flow of the initial value generation processing.

First, the shape data generator 13 performs a shape data generation processing (FIG. 12B: step S11). The shape data generation processing will be explained by using FIGS. 13 to 19.

Figure 13:
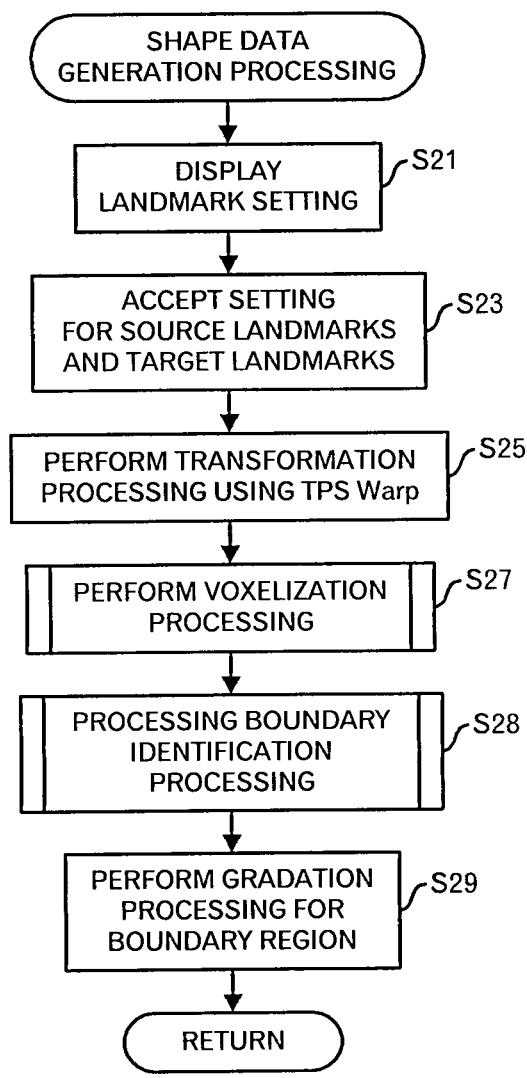
FIG. 13 is a diagram depicting a processing flow of a shape data generation processing.

The transformation processing unit 131 reads out the reference shape data from the reference shape data storage unit 20, and reads out the segment image data from the segment image data storage unit 12. Then, the transformation processing unit 131 displays a landmark setting screen that includes the reference shape data and the segment image data on a display device (FIG. 13: step S21).

The user watches the landmark setting screen that is displayed on the display device and performs rough alignment of the reference shape and the shape identified by the segment image data (hereinafter referred to the target shape). More specifically, (1) the user sets source landmarks at predetermined positions in the reference shape. (2) The user then sets target landmarks at positions in the target shape, which correspond to the positions where the source landmarks are set. The predetermined positions are, for example, characteristic positions of the left ventricular fluid.

The transformation processing unit 131 accepts settings for the source landmarks and the target landmarks, and stores the data for the source landmarks and the target landmarks (e.g. three-dimensional coordinates) in a storage device such as a main memory or the like (step S23).

The transformation processing unit 131 performs a processing to transform the reference shape by using a method such as Thin Plate Spline (TPS) Warp, which will be described later (step S25). The transformation processing unit 131 then stores the shape data, which is the processing result, in the first shape data storage unit 132. The format of the shape data, which is the processing result, is the format of the STL data.

Figure 14:
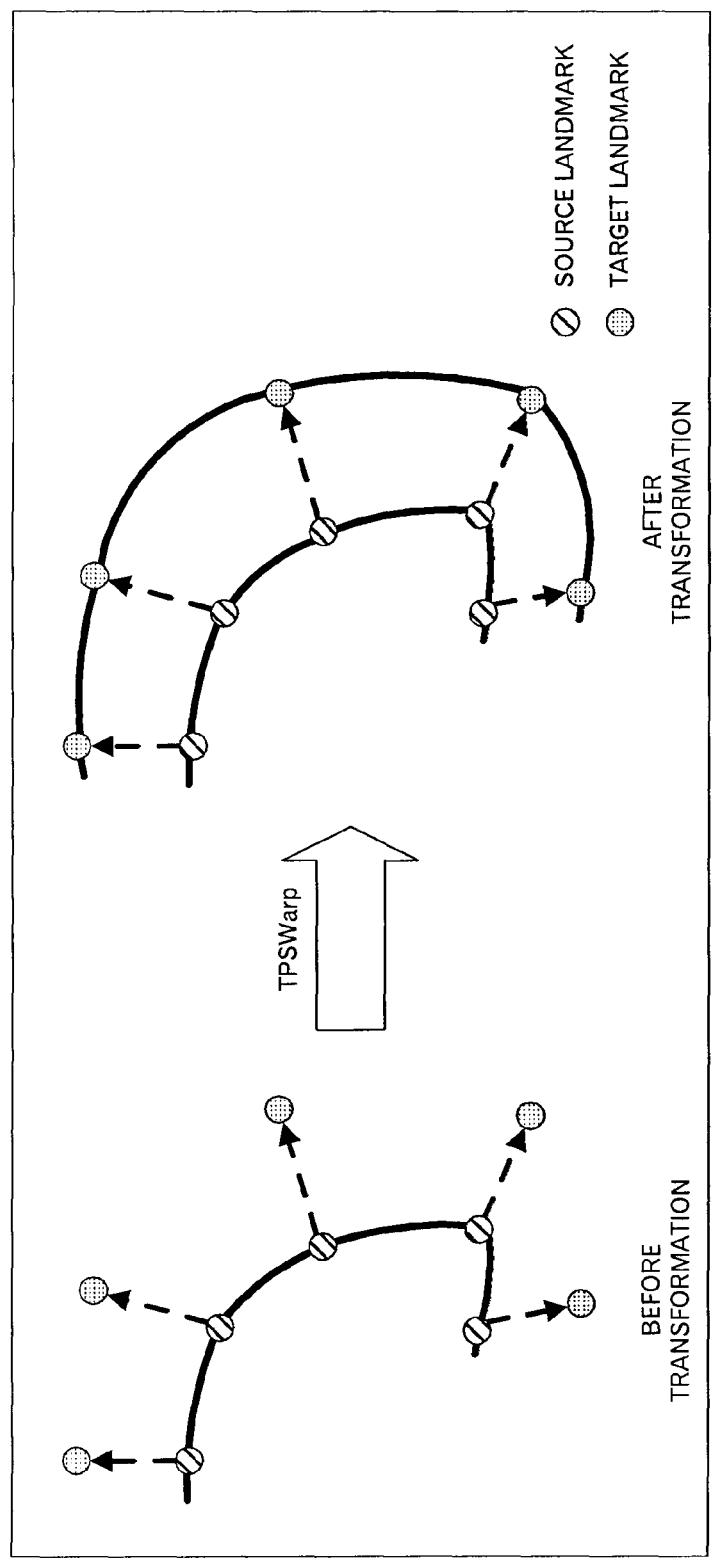
FIG. 14 is a diagram to explain TPS (Thin Plate Spline) Warp.

Here, the TPS Warp will be explained. As illustrated in FIG. 14, in the TPS Warp, when the source landmarks and the target landmarks that correspond to the source landmarks are given, the transformation is performed so that the source landmarks lay on the corresponding target landmarks. As for the TPS Warp, the entire contents of "Fred L. Bookstein, "Principal Warps: Thin-Plate Splines and the Decomposition of Deformations", IEEE TRANSACTIONS ON PATTERN ANALYSIS AND MACHINE INTELLIGENCE, VOL. 11, NO. 6, PP. 567-585, JUNE 1989" are incorporated herein by reference.

Thus, the reference shape can be transformed to match the region designated by the user.

Then, the voxelization processing unit 133 uses the shape data that is stored in the first shape data storage unit 132 to perform a voxelization processing (step S27). The voxelization processing will be explained by using FIGS. 15A to 17.

First, some prerequisite matters for explanation of the voxelization processing are explained.

The following represents a voxel value at coordinates (x, y, z) in the voxel space.

$$V(x,y,z)$$

The initial value is −1.

The following represents voxels in the voxel space.

$$\{v_i\}_{i=1,\ldots,vN}$$

vN represents the number of voxels included in the voxel space. In the voxel space, xN represents the number of voxels in the x-axis direction, yN represents the number of voxels in the y-axis direction, and zN represents the number of voxels in the z-axis direction. Therefore, xN*yN*zN=vN holds.

The following represents lower limit (lower left) coordinates in the voxel space.

$$L=(x_L,y_L,z_L)^T$$

The following represents upper limit (upper right) coordinates in the voxel space.

$$U=(x_U,y_U,z_U)^T$$

The following represents the size (xs*ys*zs) of the voxel.

$$vs = \begin{pmatrix} xs & 0 & 0 \\ 0 & ys & 0 \\ 0 & 0 & zs \end{pmatrix}$$

Regard the shape data stored in the first shape data storage unit 132 as S, and the shape data S is defined as follows.

$$\{\{p_i\}_{i=1,\ldots,N},\{m_j\}_{j=1,\ldots,M}\}$$

Here, $\{p_i\}_{i=1,\ldots,N}$ represents vertices of the shape data S, and a vector $\{m_j\}_{j=1,\ldots,M}$ represents triangular mesh of the shape data S. N represents the number of the vertices of the shape data S. M represents the number of the triangular mesh elements of the shape data S.

A vertex included in the mesh $m_j$ is defined as follows.

$$\{p_{m_j,i} := (x_{m_j,i}, y_{m_j,i}, z_{m_j,i})^T\}_{i=1,2,3}$$

The voxel space generated by the voxelization processing is a voxel space that corresponds to a voxel space identified by the tomographic image data stored in the tomographic image data storage unit 10. In other words, the coordinates of the lower limit and the upper limit, the number of the voxels in each axis direction, and the size of the voxel are the same.

A processing flow of the voxelization processing will be explained later.

Figure 15A:
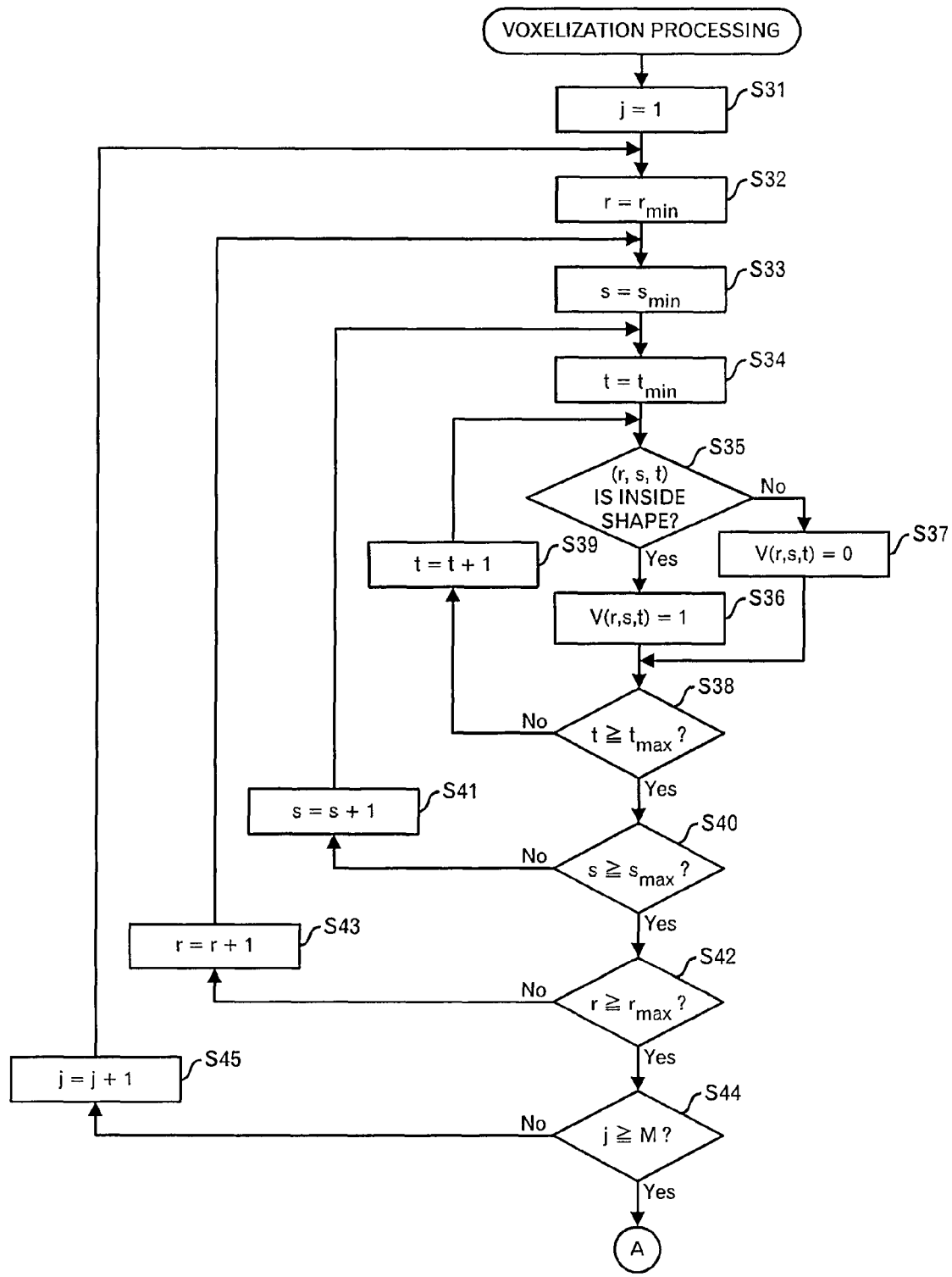
FIG. 15A is a diagram depicting a processing flow of a voxelization processing.

First, the voxelization processing unit 133 sets a variable j for identifying the triangular mesh elements as j=1 (FIG. 15A: step S31).

The voxelization processing unit 133 sets a variable r that represents the x-coordinate in the voxel space as r=$r_{min}$ (step S32). $r_{min}$ is a value described below.

$$r_{min} = \left\lfloor \frac{\min_i\{x_{m_j,i}\} - x_L}{xs} \right\rfloor$$

Here, the first member of the numerator in the Gauss symbol is a function to obtain a minimum of $x_{m(j),1}$ ((j) represents that j is a subscript of m).

The voxelization processing unit 133 sets a variable s that represents the y-coordinate in the voxel space as s=$s_{min}$ (step S33). $s_{min}$ is a value described below.

$$s_{min} = \left\lfloor \frac{\min_i\{y_{m_j,i}\} - y_L}{ys} \right\rfloor$$

The voxelization processing unit 133 sets a variable t that represents the z-coordinate in the voxel space as t=$t_{min}$ (step S34). $t_{min}$ is a value described below.

$$t_{min} = \left\lfloor \frac{\min_i\{z_{m_j,i}\} - z_L}{zs} \right\rfloor$$

The voxelization processing unit 133 determines whether (r, s, t) is located inside the shape data S (step S35). At the step S35, it is determined whether the following expression is satisfied.

$$((vs \cdot v + L) - p_{m_j,1}) \cdot ((p_{m_j,2} - p_{m_j,1}) \times (p_{m_j,3} - p_{m_j,1}))$$

Here, v is defined as described below.

$$v=(r,s,t)^T$$

At the aforementioned expression, $((vs \cdot v + L) - p_{m(j),1})$ ((j) represents that j is a subscript of m) represents a vector whose start point is $p_{m(j),1}$ and end point is the voxel (r, s, t). $((p_{m(j),2} - p_{m(j),1}) \times (p_{m(j),3} - p_{m(j),1}))$ represents a normal vector that passes through a plane which includes the triangular mesh element from the inside of the shape to the outside of the shape. "×" represents a cross product. By determining whether an inner product between the former vector and the normal vector is less than 0 or not, it can be determined whether the voxel (r, s, t) is located inside the shape data S or not. However, determination target voxels at the processing of the step S35 is limited to voxels which are located near the boundary between the left ventricular fluid and a part which is not the left ventricular fluid.

When it is determined that the (r, s, t) is located inside the shape data S (step S35: Yes route), the voxelization processing unit 133 sets V (r, s, t)=1 (step S36). On the other hand, when it is determined that the (r, s, t) is not located inside the shape data S (step S35: No route), the voxelization processing unit 133 sets V (r, s, t)=0 (step S37).

The voxelization processing unit 133 determines whether t≥$t_{max}$ holds (step S38). $t_{max}$ is a value described below.

$$t_{max} = \left\lfloor \frac{\max_i\{z_{m_j,i}\} - z_L}{zs} \right\rfloor$$

Here, the first member of the numerator in the Gauss symbol is a function to obtain the maximum of $z_{m(j),1}$ ((j) represents that j is a subscript of m).

When it is determined that t≥$t_{max}$ does not hold (step S38: No route), the voxelization processing unit 133 increments the coefficient t by "1" (step S39), and the processing returns to the processing of the step S35. On the other hand, when it is determined that t≥$t_{max}$ holds (step S38: Yes route), the voxelization processing unit 133 determines whether s≥$s_{max}$ holds (step S40). $s_{max}$ is a value described below.

$$s_{max} = \left\lfloor \frac{\max_i \{y_{m_j,i}\} - y_L}{ys} \right\rfloor$$

When it is determined that $s \geq s_{max}$ does not hold (step S40: No route), the voxelization processing unit 133 increments the coefficient s by "1" (step S41), and the processing returns to the processing of the step S34. On the other hand, when it is determined that $s \geq s_{max}$ holds (step S40: Yes route), the voxelization processing unit 133 determines whether $r \geq r_{max}$ holds (step S42). $r_{max}$ is a value described below.

$$r_{max} = \left\lfloor \frac{\max_i \{x_{m_j,i}\} - x_L}{xs} \right\rfloor$$

When it is determined that $r \geq r_{max}$ does not hold (step S42: No route), the voxelization processing unit 133 increments the coefficient r by "1" (step S43), and the processing returns to the processing of the step S33. On the other hand, when it is determined that $r \geq r_{max}$ holds (step S42: Yes route), the voxelization processing unit 133 determines whether $j \geq M$ holds (step S44). When it is determined that $j \geq M$ does not hold (step S44: No route), the voxelization processing unit 133 increments the coefficient j by "1" (step S45), and the processing returns to the processing of the step S32. On the other hand, when it is determined that $j \geq M$ holds (step S44: Yes route), the processing shifts to the step S51 in FIG. 16A through a terminal A.

Figure 15B:
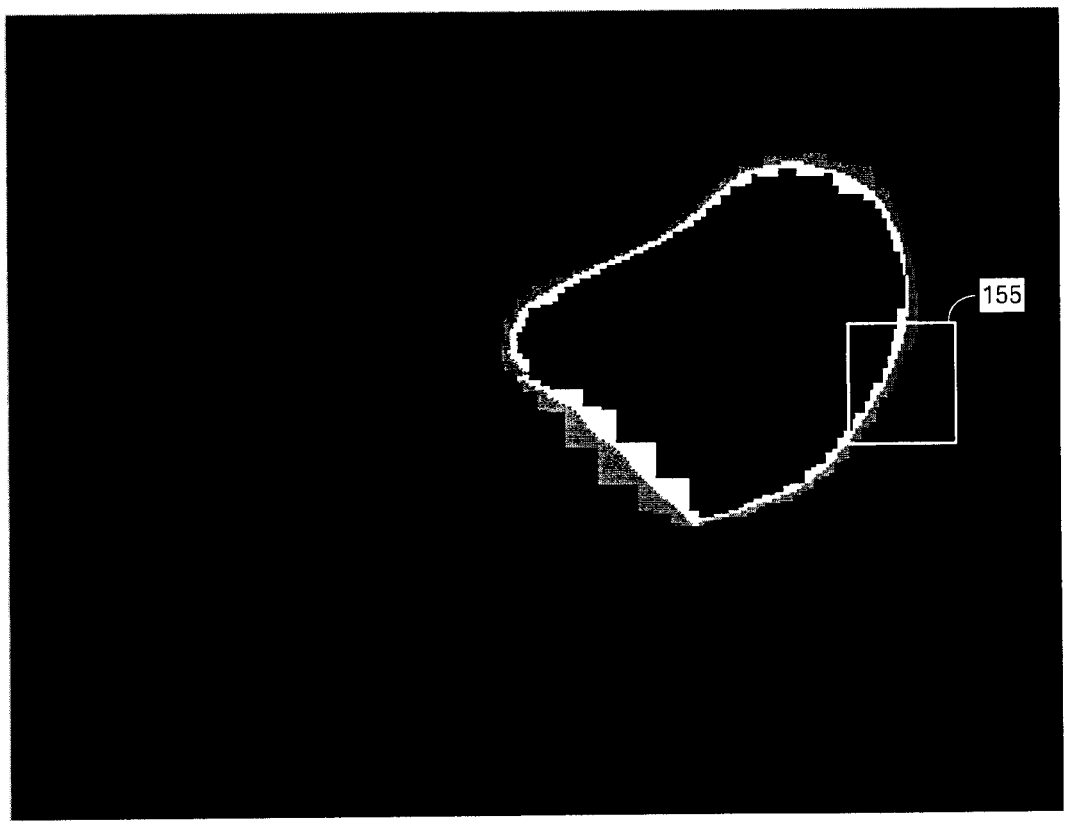
FIG. 15B is a diagram depicting an example of data generated in the process of the voxelization processing.

FIG. 15B illustrates an example of the voxel data generated by the processings described above. FIG. 15B illustrates a voxel value at a specific z-coordinate. In FIG. 15B, a voxel whose voxel value is 1 is illustrated in white, a voxel whose voxel value is 0 is illustrated in gray, and a voxel whose voxel value is −1 is illustrated in black. In the processings described above, voxels except voxels which are located near the boundary between the left ventricular fluid and the part which is not the left ventricular fluid remain set their initial value "−1".

Figure 15C:
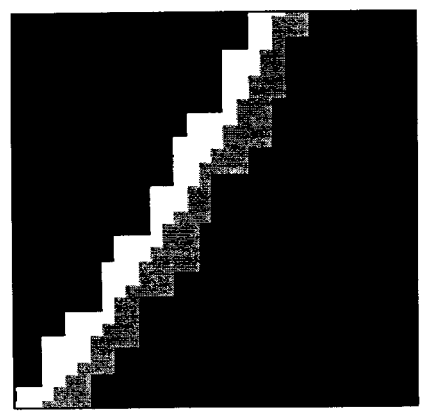
FIG. 15C is a diagram depicting an example of data generated in the process of the voxelization processing.

FIG. 15C is an enlarged view of a region surrounded by a white line 155 in FIG. 15B. As illustrated in FIG. 15C, voxel values of the voxels, which are located inside the shape data S, among the voxels which are located near the boundary are 1, and voxel values of the voxels, which are located outside the shape data S, among the voxels which are located near the boundary are 0.

Figure 16A:
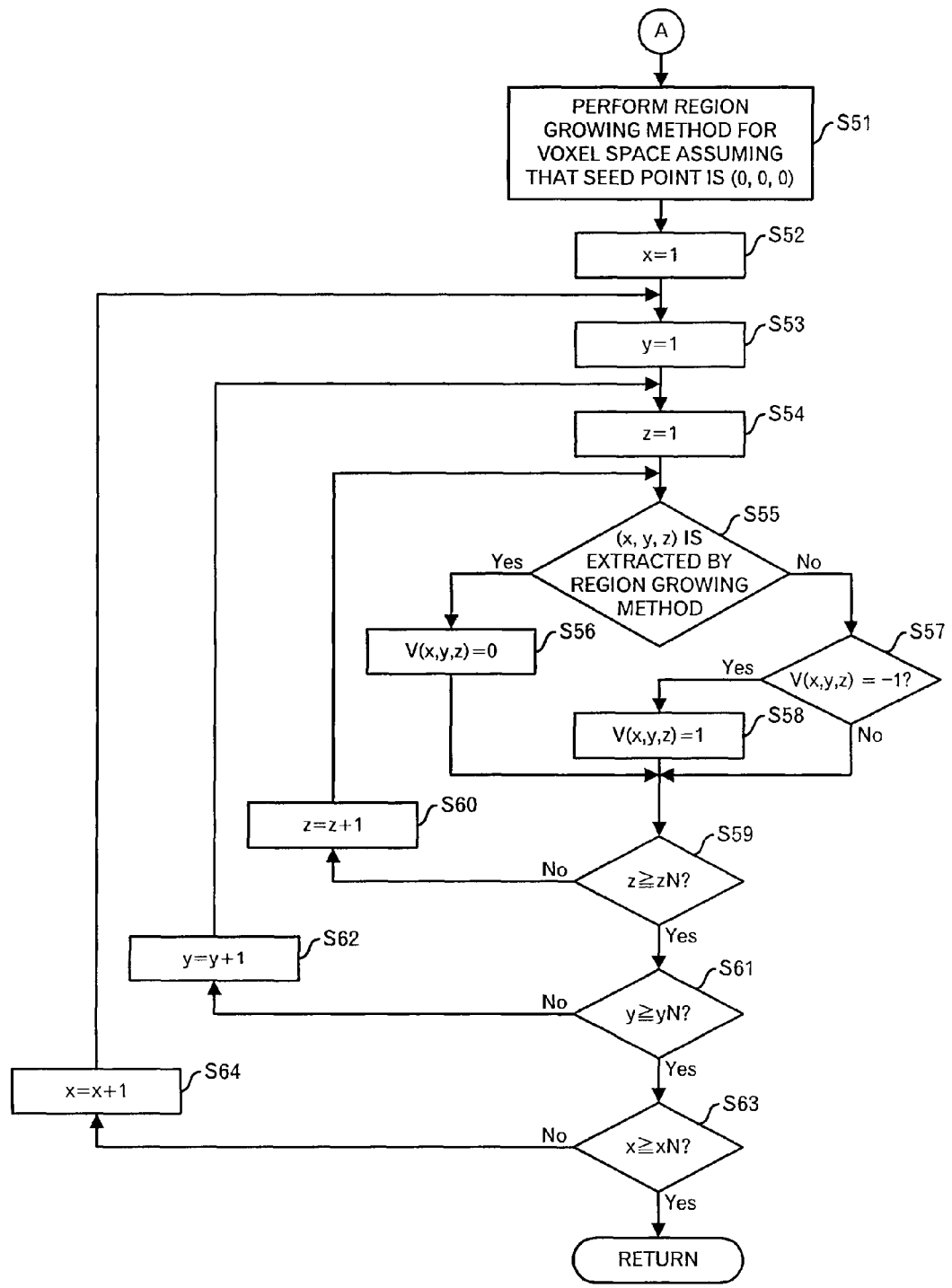
FIG. 16A is a diagram depicting a processing flow of the voxelization processing.

Shifting to the explanation of FIG. 16A, the voxelization processing unit 133 performs the region growing method for the voxel space assuming that a seed point is (0, 0, 0) (FIG. 16A: step S51), and stores the processing result in a storage device such as a main memory or the like. The region growing method is a method for expanding a region by involving points which connect to the seed point and extracting a target region. As for the region growing method, the entire contents of "A. Tremeau, N. Borel, "A Region Growing and Merging Algorithm to Color Segmentation", Pattern recognition, Volume 30, Issue 7, July 1997, Pages 1191-1203" are incorporated herein by reference. At the step S51, the seed point is (0, 0, 0), but if a voxel is a part which is not the left ventricular fluid (in other words, a part of the outside of the shape data S), the voxel may be used as the seed point.

The voxelization processing unit 133 sets a variable x for identifying the x-coordinate as x=1 (step S52).

The voxelization processing unit 133 sets a variable y for identifying the y-coordinate as y=1 (step S53).

The voxelization processing unit 133 sets a variable z for identifying the z-coordinate as z=1 (step S54).

The voxelization processing unit 133 determines whether the voxel (x, y, z) has been extracted by the region growing method (step S55). When it is determined that the voxel (x, y, z) has been extracted by the region growing method (step S55: Yes route), the voxel (x, y, z) is located outside of the shape data S. Then, the voxelization processing unit 133 sets V (x, y, z)=0 (step S56). When it is determined that the voxel (x, y, z) has not been extracted by the region growing method (step S55: No route), the voxelization processing unit 133 determines whether V (x, y, z) is −1 (step S57).

When it is determined that V (x, y, z) is −1 (step S57: Yes route), the voxel (x, y, z) is located inside of the shape data S and its value remains the initial value. Then, the voxelization processing unit 133 sets V (x, y, z)=1 (step S58). On the other hand, when it is determined that V (x, y, z) is not −1 (step S57: No route), V (x, y, z) has already been set as V (x, y, z)=0 or 1. Then, the processing shifts to the processing of the step S59.

The voxelization processing unit 133 determines whether $z \geq zN$ holds (step S59). When it is determined that $z \geq zN$ does not hold (step S59: No route), the voxelization processing unit 133 increments the coefficient z by "1" (step S60), and the processing returns to the processing of the step S55.

When it is determined that $z \geq zN$ holds (step S59: Yes route), the voxelization processing unit 133 determines whether $y \geq yN$ holds (step S61). When it is determined that $y \geq yN$ does not hold (step S61: No route), the voxelization processing unit 133 increments the coefficient y by "1" (step S62), and the processing returns to the processing of the step S54.

When it is determined that $y \geq yN$ holds (step S61: Yes route), the voxelization processing unit 133 determines whether $x \geq xN$ holds (step S63). When it is determined that $x \geq xN$ does not hold (step S63: No route), the voxelization processing unit 133 increments the coefficient x by "1" (step S64), and the processing returns to the processing of the step S53. On the other hand, when it is determined that $x \geq xN$ holds (step S63: Yes route), the processing returns to the calling-source processing.

Figure 16B:
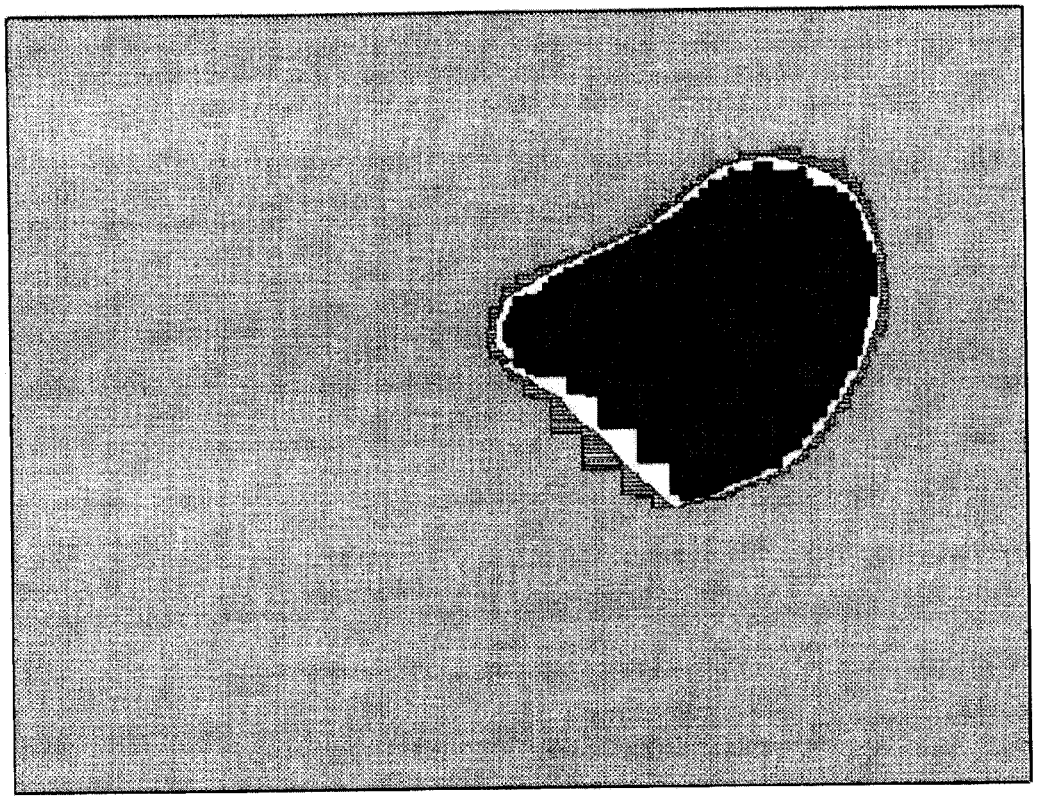
FIG. 16B is a diagram depicting an example of data generated in the process of the voxelization processing.

The processing of the step S56 will be explained by using FIG. 16B. In this embodiment, since the seed point is (0, 0, 0) (in other words, the seed point is in the part of the outside of the shape data S), the part of the outside of the shape data S is extracted by the region growing method. Therefore, when the voxel value extracted by the region growing method is regarded as 0 at the step S56, the part is extracted as illustrated in FIG. 16B. FIG. 16B illustrates a voxel value in a specific z-coordinate as well as FIG. 15B, a voxel whose voxel value is 1 is illustrated in white, a voxel whose voxel value is 0 is illustrated in gray, and a voxel whose voxel value is −1 is illustrated in black. However, voxels which were set as V (x, y, z)=0 at the processing of the step S37 is illustrated in gray with black stripes. Then, values of voxels that correspond to a black part inside the shape data S in FIG. 16B are substituted with 1 by the processing of the step S58. Therefore, the values of voxels inside the shape data S become 1, and the values of voxels outside the shape data S become 0.

Figure 17:
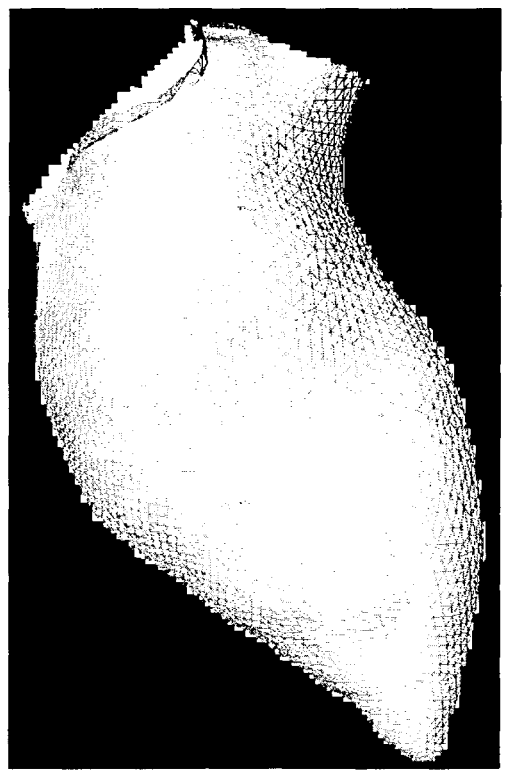
FIG. 17 is a diagram depicting data generated by the voxelization processing.

By performing the voxelization processing as described above, the shape data which was STL data becomes data in the voxel space. By performing the voxelization processing, for example, data as illustrated in FIG. 17 can be generated. In FIG. 17, a part whose voxel values are 1 is illustrated in bright color (white), and a part whose voxel values are 0 is illustrated in black. In this stage, since the voxel values on the boundary between the left ventricular fluid and the part which is not the left ventricular fluid are 0 or 1, the boundary is not smooth but convexo-concave.

Returning to the explanation of FIG. 13, when the voxelization processing (step S27) ends, the boundary identification unit 135 performs a boundary identification processing (step S28). The boundary identification processing will be explained by using FIG. 18.

Figure 18:
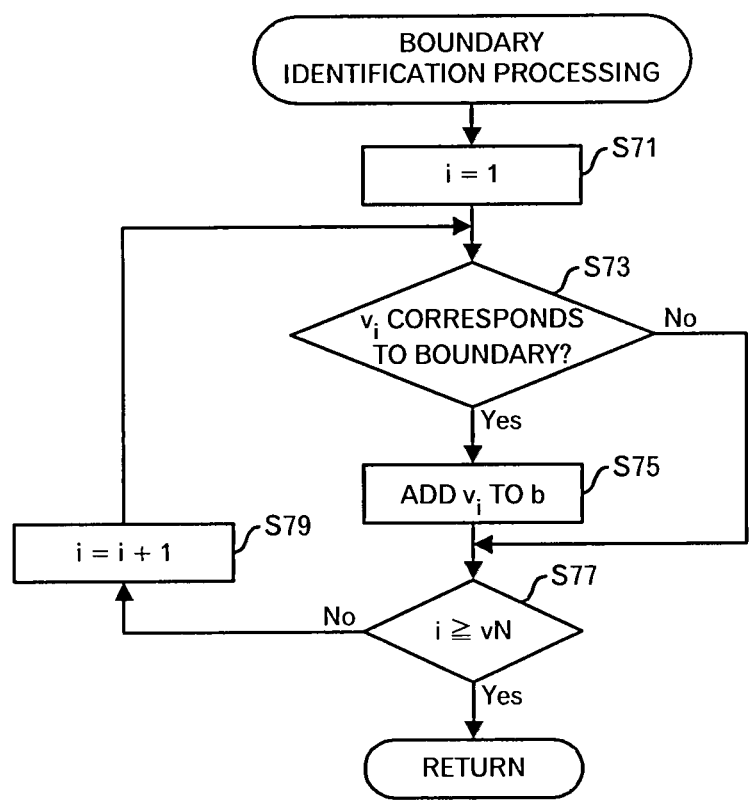
FIG. 18 is a diagram depicting a processing flow of a boundary identification processing.

First, the boundary identification unit 135 sets a variable i for identifying voxels as i=1 (FIG. 18: step S71).

The boundary identification unit 135 determines whether $v_i$ corresponds to the boundary between the left ventricular fluid and a part which is not the left ventricular fluid (step S73). At the step S73, it is determined whether the following expression is satisfied.

$$|V(x,y,z)-V(x+1,y,z)|+|V(x,y,z)-V(x-1,y,z)|+|V(x,y,z)-V(x,y+1,z)|+|V(x,y,z)-V(x,y-1,z)|+|V(x,y,z)-V(x,y,z+1)|+|V(x,y,z)-V(x,y,z-1)|>0$$

When it is determined that $v_i$ corresponds to the boundary (step S73: Yes route), the boundary identification unit 135 adds $v_i=(x,y,z)$ to boundary $b=\{v_b\}$ (step S75), and stores the coordinates of $v_i=(x,y,z)$ in the identification result storage unit 136. When it is determined that $v_i$ does not correspond to the boundary (step S73: No route), the processing shifts to the processing of the step S77.

The boundary identification unit 135 determines whether i≥vN holds (step S77). When it is determined that i≥vN does not hold (step S77: No route), the boundary identification unit 135 increments the coefficient i by "1" (step S79), and the processing returns to the processing of the step S73. On the other hand, when it is determined that i≥vN holds (step S77: Yes route), the processing returns to the calling-source processing.

Thus, if voxels that correspond to the boundary are identified, it is possible to use the voxels for the gradation processing.

Returning to the explanation of FIG. 13, the gradation processing unit 137 performs the gradation processing to a boundary of a shape identified by data stored in the voxelization data storage unit 134, and stores the processing result in the second shape data storage unit 138 (step S29). Then, the processing returns to the calling-source processing.

Figure 19:
FIG. 19 is a diagram depicting data generated by a gradation processing.

At the step S29, a Gaussian filter is applied so that an average of values of voxels, whose data is stored in the identification result storage unit 136, becomes 0.5 (in other words, an average of 0 and 1). When the Gaussian filter is applied, a distribution of the voxel values is obtained as illustrated in FIG. 19. In FIG. 19, the voxel values are in the range from 0 to 1, and the larger the voxel value is, the brighter the color is. On the boundary, the voxel value gradually changes from 1 to 0.

Returning to the explanation of the FIG. 12B, and when the shape data generation processing ends, the probability map generator 14 performs a probability map generation processing (step S13). The probability map generation processing will be explained by using FIGS. 20 to 25.

Figure 20:
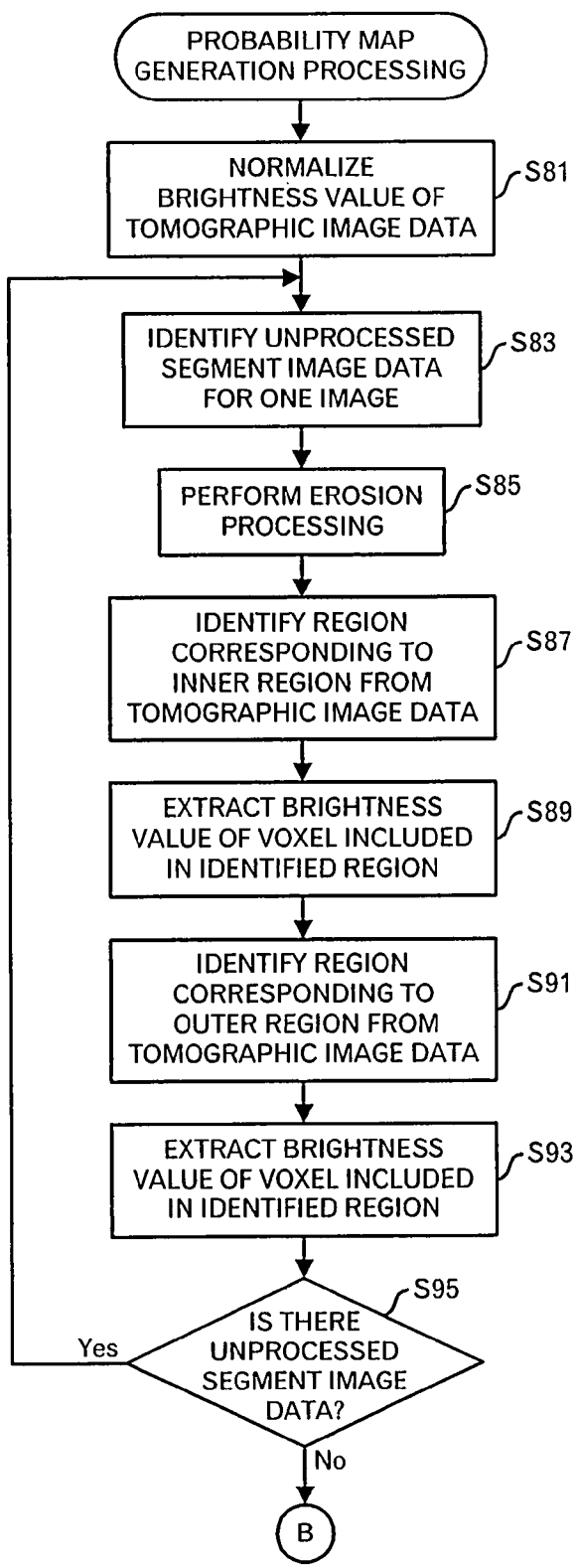
FIG. 20 is a diagram depicting a processing flow of a probability map generation processing.

First, the normalization unit 141 performs a processing to normalize brightness values of tomographic image data stored in the tomographic image data storage unit 10, and stores the processing result in the first data storage unit 142 (FIG. 20: step S81). At the step S81, for example, the brightness value is normalized between −1000 and 1000. However, the brightness value is not limited to the range of such values.

The morphology processing unit 143 in the histogram generator 150 identifies data of an unprocessed segment image from the segment image data storage unit 12 (step S83).

The morphology processing unit 143 performs an erosion processing, which is a kind of a morphology processing, to the identified segment image data, and stores the processing result in the second data storage unit 144 (step S85). As for the morphology processing, the entire contents of "L. Vincent, "Morphological grayscale reconstruction in image analysis: Applications and efficient algorithms", IEEE Transactions on Image Processing, 2(2): 176-201, 1993." are incorporated herein by reference.

Figure 21:
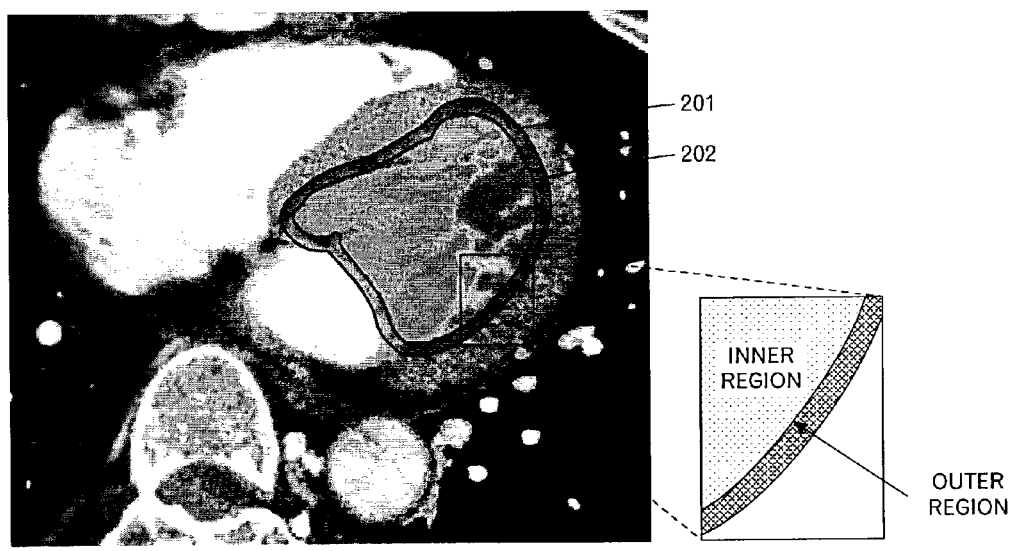
FIG. 21 is a diagram to explain an erosion processing.

The erosion processing of the step S85 will be explained by using FIG. 21. In FIG. 21, a region surrounded by a curve 202 (hereinafter referred to an inner region) is a region designated by a user. The erosion processing of the step S85 masks the region designated by the user by a region surrounded by a curve 201. Hereinafter, a region between the curve 201 and the curve 202 is called an outer region.

The brightness value extraction unit 145 identifies, from the tomographic image data which corresponds to the segment image data stored in the first data storage unit 142, a region which corresponds to the inner region in the segment image data identified at the step S83 (step S87).

The brightness value extraction unit 145 extracts brightness values of voxels included in the region identified at the step S87, and stores the brightness values in the brightness value storage unit 149 (step S89).

Figures 22, 23:
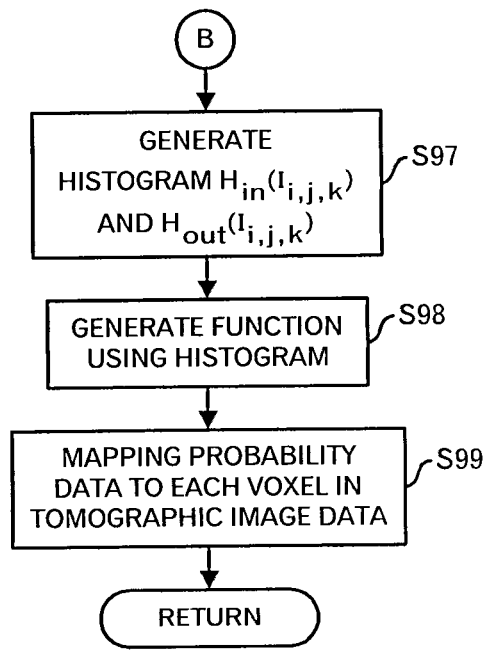
FIG. 22 is a diagram depicting an example of data stored in a brightness value storage unit.
FIG. 23 is a diagram depicting a processing flow of the probability map generation processing.

FIG. 22 illustrates an example of data stored in the brightness value storage unit 149. In the example of FIG. 22, for the inner region and the outer region, coordinates of a voxel in the tomographic image data and a brightness value of the voxel are stored.

The brightness value extraction unit 145 identifies, from the tomographic image data which corresponds to the segment image data stored in the first data storage unit 142, a region which corresponds to the outer region in the segment image data identified at the step S83 (step S91).

The brightness value extraction unit 145 extracts brightness values of voxels included in the region identified at the step S91, and stores the brightness values in the brightness value storage unit 149 (step S93).

The brightness value extraction unit 145 determines whether there is unprocessed segment image data in the segment image data storage unit 12 (step S95). When it is determined that there is the unprocessed segment image data (step S95: Yes route), the processing returns to the processing of the step S83 to perform a processing to the following segment image data. On the other hand, when it is determined that there is no unprocessed segment image data (step S95: No route), the processing shifts to the step S97 in FIG. 23 through a terminal B.

Shifting to the explanation of FIG. 23, the brightness value extraction unit 145 uses brightness values stored in the brightness value storage unit 149 to generate a histogram $H_{in}(I_{i,j,k})$ for the inner region and a histogram $H_{out}(I_{i,j,k})$ for the outer region (step S97). Then, the brightness value extraction unit 145 stores the generated histograms in the histogram data storage unit 146.

Figure 24:
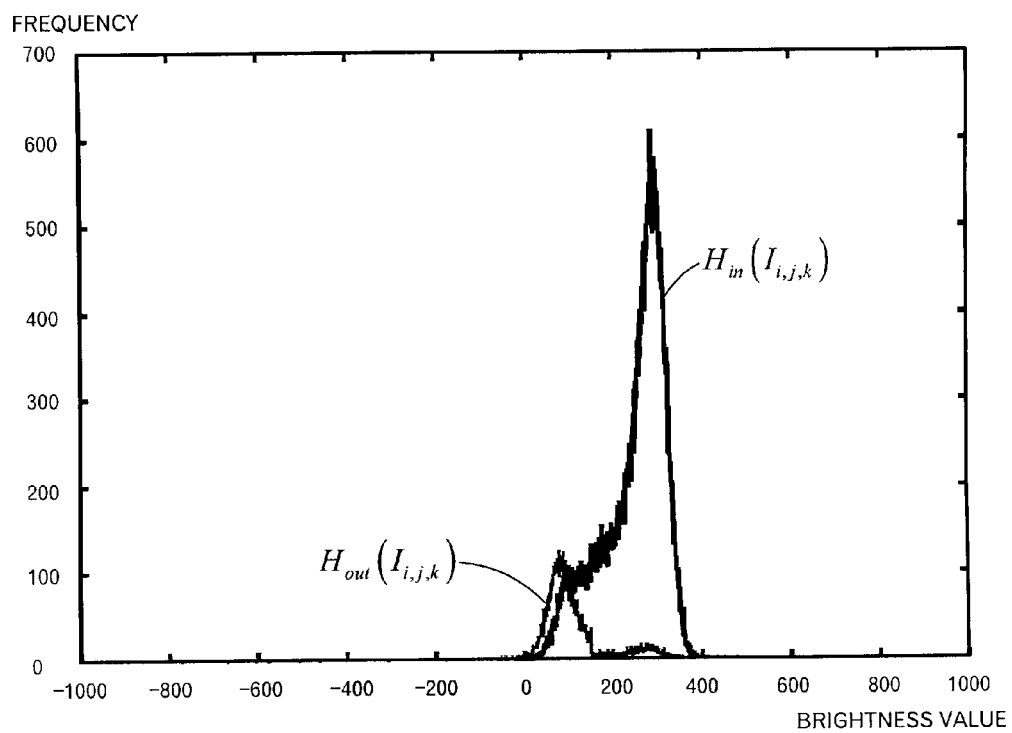
FIG. 24 is a diagram depicting a histogram for an inner region and a histogram for an outer region.

FIG. 24 illustrates the histograms generated at the step S97. In FIG. 24, a vertical axis represents a frequency, and a horizontal axis represents a brightness value. The histogram $H_{in}(I_{i,j,k})$ for the inner region has a peak of the brightness values in the proximity of 300. On the other hand, the histogram $H_{out}(I_{i,j,k})$ for the outer region has a peak of the brightness values in the proximity of 70.

The mapping unit 147 uses the histograms stored in the histogram data storage unit 146 to generate a function (step S98). Moreover, the mapping unit 147 maps probability data to each voxel in the tomographic image data by using the generated function (step S99). Then, the mapping unit 147 stores the mapping result in the probability map storage unit 148. Then, the processing returns to the calling-source processing. At the step S99, the following function is used for mapping.

$$\frac{H_{in}(I_{i,j,k})}{H_{in}(I_{i,j,k}) + H_{out}(I_{i,j,k})} \quad (H_{in}(I_{i,j,k}) + H_{out}(I_{i,j,i}) \neq 0)$$

$$0.5 \quad (H_{in}(I_{i,j,k}) + H_{out}(I_{i,j,i}) = 0)$$

Figure 25:
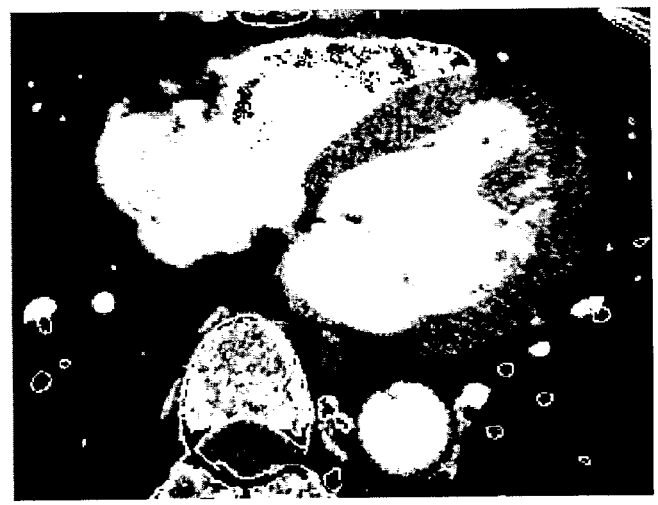
FIG. 25 is a diagram depicting a result of the probability map generation processing for a specific z coordinate.

A probability calculated by the aforementioned expression represents a probability that a voxel (i, j, k) in the tomographic image data is included in the left ventricular fluid. FIG. 25 illustrates an example of data generated by the probability map generation processing. FIG. 25 illustrates probability data in a specific z-coordinate. In FIG. 25, the closer the probability is to 1, the brighter the color is, and the closer the probability is to 0, the darker the color is. In this embodiment, since the probability map for the left ventricular fluid is generated, a probability for a region except the left ventricular fluid in FIG. 25 carries no significance.

Returning to the explanation of FIG. 12B, when the probability map generation processing ends, and the merging unit 15 generates initial values by merging data stored in the second shape data storage unit 138 and probability data stored in the probability map storage unit 148 (step S15). Then, the merging unit 15 stores the generated initial values in the initial value storage unit 16, and the processing returns to the calling-source processing. At the step S15, the initial values are generated according to the following expression.

$$(1-\lambda)D1_{i,j,k} + \lambda D2_{i,j,k} \quad (D1_{i,j,k} > esp)$$

$$0 \quad (D1_{i,j,k} < esp)$$

Here, $\lambda$ represents a value in the range $0 < \lambda < 1$, for example 0.5. $D1_{i,j,k}$ represents a voxel value of the voxel (i, j, k), which is stored in the second shape data storage unit 138. $D2_{i,j,k}$ represents probability data of the voxel (i, j, k), which is stored in the probability map storage unit 148. eps represents a sufficiently-small value, for example 0.01.

Figure 26:
FIG. 26 is a diagram depicting a result of the initial value generation processing for the specific z coordinate.

FIG. 26 illustrates an example of the initial values generated at the step S15. FIG. 26 illustrates initial values in a specific z-coordinate. In FIG. 26, the closer the value is to 1, the brighter the color is, and the closer the value is to 0, the darker the color is. Moreover, since a condition of eps is used in the aforementioned expression, a region regarded as a region except the left ventricular fluid is removed (in other words, the initial values are 0).

Returning to the explanation of FIG. 11, the region extraction unit 17 uses initial values stored in the initial value storage unit 16 to perform a region extraction processing (step S7), and stores the processing result in the extraction result storage unit 18.

At the step S7, a region of the left ventricular fluid is extracted by filtering, by using the following reaction-diffusion equation, initial values stored in the initial value storage unit 16.

$$\frac{\partial u}{\partial t} = \alpha f(u) + \beta \Delta u$$

Here, u represents a voxel value. $\alpha$ represents a reaction coefficient, and $\beta$ represents a diffusion coefficient.

The first member represents a reaction member, and the following function is used.

$$f(u) = -\sin(2\pi u)$$

The reaction member has an effect to concentrate u on a representative value. In case of the reaction-diffusion equation described above, when u is a value in the range from 0 to 0.5, u gradually approaches 0. When u is a value in the range from 0.5 to 1, u gradually approaches 1.

The second member represents a diffusion member, and has an effect similar to that of the Gaussian filter (in other words, an effect for smoothing).

The aforementioned reaction-diffusion equation is discretized as follows.

$$u_{i,j,k}^{n+1} = u_{i,j,k}^n + \Delta t(\alpha \cdot f(u_{i,j,k}^n) + \beta \cdot (D^{2x} + D^{2y} + D^{2z})u_{i,j,k}^n)$$

Here, $u_{i,j,k}$ represents a voxel value of the voxel (i, j, k). D is expressed as follows.

$$D^{2x}u_{i,j,k}^n = \frac{D^{+x}u_{i,j,k}^n - D^{-x}u_{i,j,k}^n}{2\Delta x}$$

$$D^{2y}u_{i,j,k}^n = \frac{D^{+y}u_{i,j,k}^n - D^{-y}u_{i,j,k}^n}{2\Delta y}$$

$$D^{2z}u_{i,j,k}^n = \frac{D^{+z}u_{i,j,k}^n - D^{-z}u_{i,j,k}^n}{2\Delta z}$$

$$D^{+x}u_{i,j,k}^n = \frac{u_{i+1,j,k}^n - u_{i,j,k}^n}{\Delta x}$$

$$D^{-x}u_{i,j,k}^n = \frac{u_{i+1,j,k}^n - u_{i,j,k}^n}{\Delta x}$$

$$D^{+y}u_{i,j,k}^n = \frac{u_{i+1,j,k}^n - u_{i,j,k}^n}{\Delta y}$$

$$D^{-y}u_{i,j,k}^n = \frac{u_{i+1,j,k}^n - u_{i,j,k}^n}{\Delta y}$$

$$D^{+z}u_{i,j,k}^n = \frac{u_{i+1,j,k}^n - u_{i,j,k}^n}{\Delta z}$$

$$D^{-z}u_{i,j,k}^n = \frac{u_{i+1,j,k}^n - u_{i,j,k}^n}{\Delta z}$$

Moreover, values $u_0$ of voxels on the outer edge are represented as follows.

$$\frac{\partial u_0}{\partial x} = 0$$

Values $u_1$ of voxels, which are included in a region designated in the segment image data, are represented as the Neumann boundary condition as follows.

$$u_1 = 1$$

Values $u_2$ of voxels, which are not included in the region designated in the segment image data, are represented as the Neumann boundary condition as follows.

$$u_2 = 0$$

Values $u_3$ of voxels, which correspond to a boundary between a ventricle and an atrium, are represented as the Dirichlet boundary condition as follows.

$$\frac{\partial u_3}{\partial t} = 0$$

Figure 27:
FIG. 27 is a diagram depicting a result of a region extraction processing for the specific z coordinate.

When the region extraction processing is performed in the above condition (in other words, the calculating is performed a predetermined number of times), for example, data as illustrated in FIG. 27 is obtained. FIG. 27 illustrates a voxel value in a specific z-coordinate. The voxel value approaches to 0 or 1 by the region extraction processing. Therefore, compared with the initial values illustrated in FIG. 26, the gradated part, which was located near the boundary, lessens.

Returning to the explanation of FIG. 11, the output unit 19 uses data that is stored in the extraction result storage unit 18 to generate data which represents the extracted region, and displays the data on a display device (step S9). Then, the processing ends.

Figure 28:
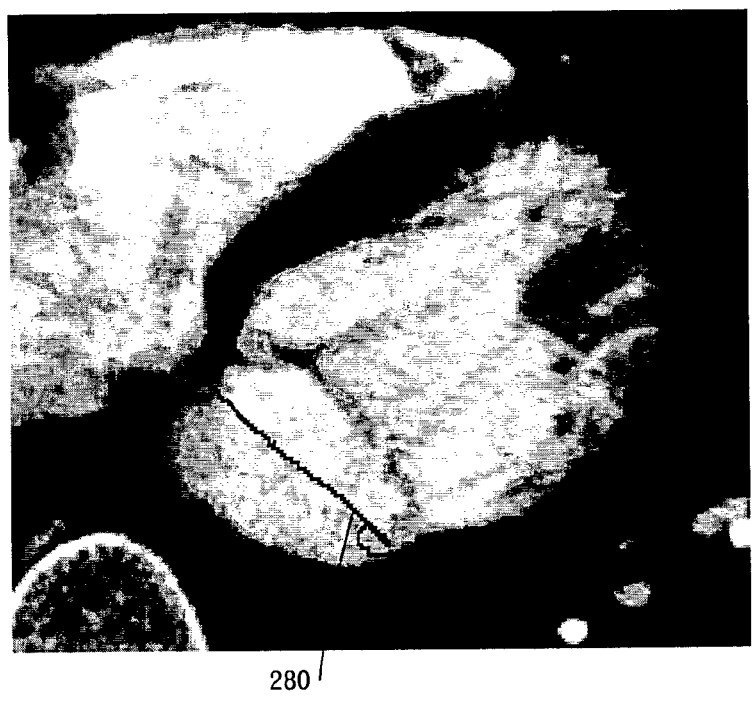
FIG. 28 is a diagram depicting an example of an image displayed on a display device.
Figure 29:
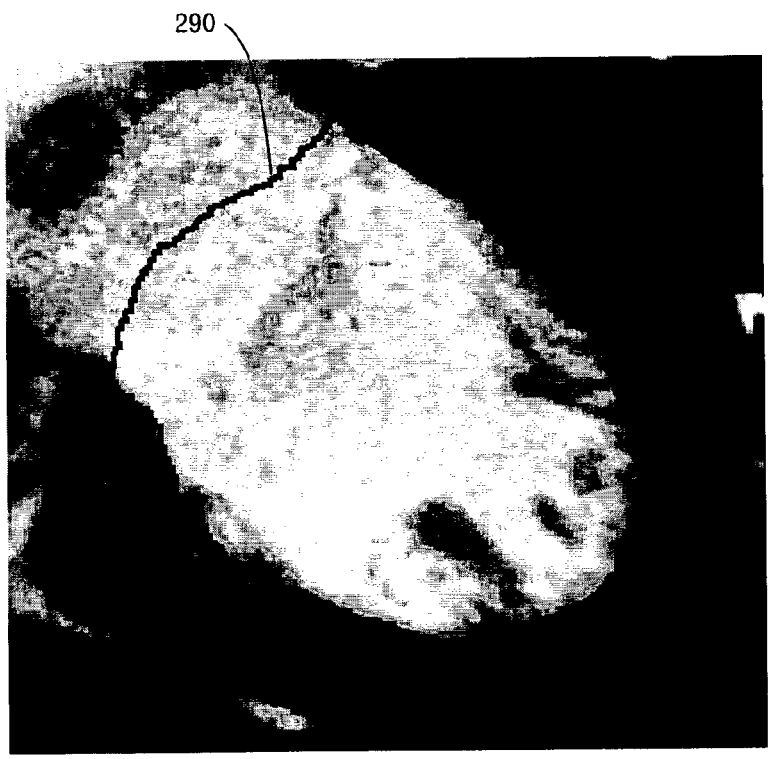
FIG. 29 is a diagram depicting an example of an image displayed on the display device.
Figure 30:
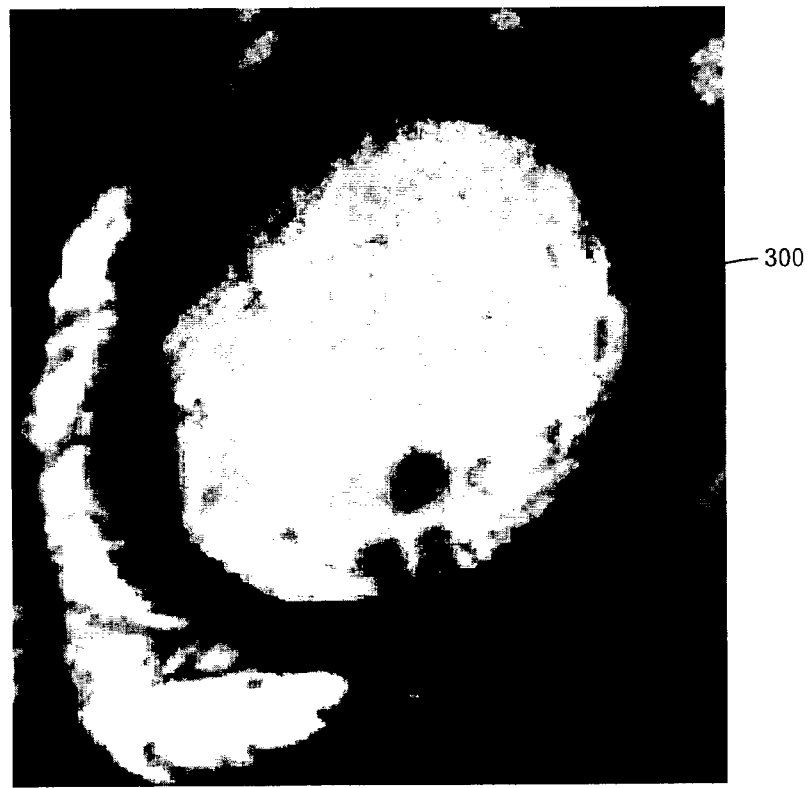
FIG. 30 is a diagram depicting an example of an image displayed on the display device.

FIGS. 28 to 30 illustrate an example of images displayed on the display device. In FIG. 28, tomographic image data in the z-coordinate, which is the same as the z-coordinate of FIG. 27, and a heavy line 280, which represents a region illustrated in FIG. 27 (a white part), are displayed so that they are superimposed. In FIG. 29, tomographic image data on the z-coordinate, which is different from the z-coordinate of FIG. 28, and a heavy line 290, which represents a region extracted by the region extraction processing, are displayed so that they are superimposed. Moreover, in FIG. 30, tomographic image data on a z-coordinate, which is different from the z-coordinates of FIG. 28 and FIG. 29, and a heavy line 300, which represents a region extracted by the region extraction processing, are displayed so that they are superimposed.

As illustrated in FIGS. 28 to 30, a portion of a papillary muscle is included in a region extracted by the region extraction processing. Moreover, unevenness due to a contrast medium disappears. In other words, a region used in a simulation, which corresponds to the left ventricular fluid, can be properly extracted in comparison with a case that the region is extracted only by brightness values.

Although the embodiments of this invention were explained, this technique is not limited to those. For example, the functional block diagram of the shape data generation apparatus 1 does not correspond to an actual program module configuration.

Moreover, as for the processing flows, as long as the processing results do not change, the turns of the processing may be exchanged or plural steps may be executed in parallel.

For example, in the initial value generation processing, although the probability map generation processing is performed after the shape data generation processing is performed, these processings can be performed in parallel.

Moreover, although the left ventricular fluid has been explained above as an example, the processings of this embodiment can be applied to another organ having a complicated shape.

Figure 31:
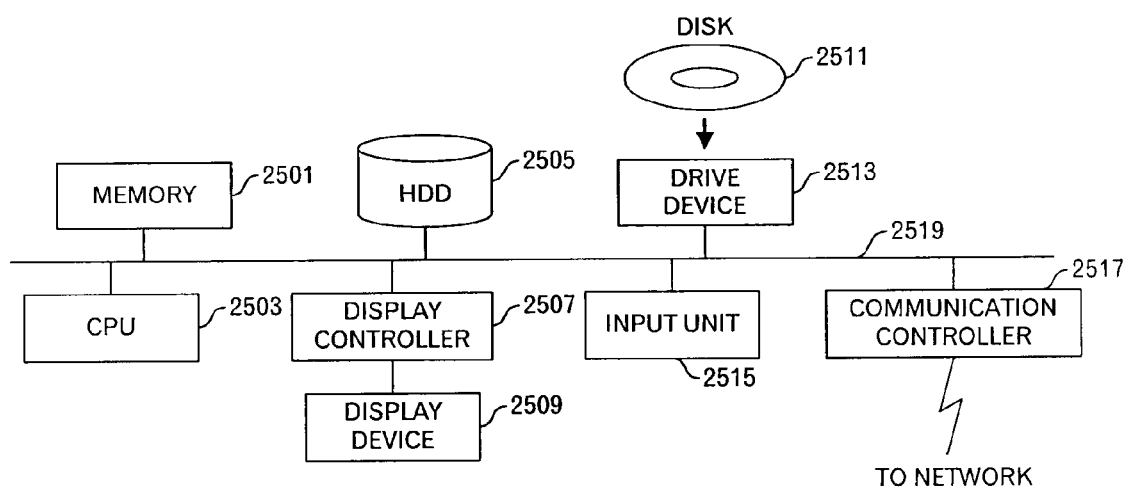
FIG. 31 is a functional block diagram of a computer.

In addition, the aforementioned shape data generation apparatus 1 is a computer device as illustrated in FIG. 31. That is, a memory 2501 (storage device), a CPU 2503 (processor), a hard disk drive (HDD) 2505, a display controller 2507 connected to a display device 2509, a drive device 2513 for a removable disk 2511, an input unit 2515, and a communication controller 2517 for connection with a network are connected through a bus 2519 as illustrated in FIG. 31. An operating system (OS) and an application program for carrying out the foregoing processing in the embodiment, are stored in the HDD 2505, and when executed by the CPU 2503, they are read out from the HDD 2505 to the memory 2501. As the need arises, the CPU 2503 controls the display controller 2507, the communication controller 2517, and the drive device 2513, and causes them to perform predetermined operations. Moreover, intermediate processing data is stored in the memory 2501, and if necessary, it is stored in the HDD 2505. In this embodiment of this technique, the application program to realize the aforementioned functions is stored in the computer-readable, non-transitory removable disk 2511 and distributed, and then it is installed into the HDD 2505 from the drive device 2513. It may be installed into the HDD 2505 via the network such as the Internet and the communication controller 2517. In the computer as stated above, the hardware such as the CPU 2503 and the memory 2501, the OS and the application programs systematically cooperate with each other, so that various functions as described above in details are realized.

The aforementioned embodiments are outlined as follows:

A shape data generation method relating to this embodiment includes: (A) first generating first three-dimensional voxel data that represents a target object by using first tomographic images, in which a first region occupied by the target object is designated, among plural tomographic images; (B) extracting, from the first tomographic images, brightness values of voxels included in the first region; second generating a function for calculating a probability that a voxel is included in the first region by using the extracted brightness values; (C) calculating, for each voxel among voxels in a voxel space that includes the plural tomographic images, a probability by using a brightness value of the voxel and the function; and (D) third generating second three-dimensional voxel data that represents the target object by using the first three-dimensional voxel data and probabilities calculated for the voxels in the voxel space.

As aforementioned above, by generating the second three-dimensional voxel data using a probability that a voxel is included in the first region, it is possible to obtain a three-dimensional shape with high accuracy.

Moreover, the extracting may include: (b1) second extracting brightness values of voxels included in a second region other than the first region, and the second generating may include: (b2) fourth generating a first frequency distribution for the brightness values of the voxels included in the first region and a second frequency distribution for the brightness values of the voxels included in the second region; fifth generating the function for calculating the probability by dividing a value of the first frequency distribution by a sum of the value of the first frequency distribution and a value of the second frequency distribution for each brightness value in the first tomographic images.

By defining the function as described here, a probability of a voxel whose brightness value is the same level as the brightness values of voxels included in the first region will become high.

Moreover, the second extracting may include: (b3) executing an erosion processing for the first region in the first tomographic images; and third extracting the brightness values from a region that is specified by the erosion processing and is other than the first region.

The region that is specified by the erosion processing will become such a region obtained by rounding out the first region. Thus, it is possible to extract brightness values of the region other than the first region properly.

Moreover, the third generating may include: (d1) second calculating a value based on a brightness value of a first voxel included in the first three-dimensional voxel data and a probability calculated for a voxel that corresponds to the first voxel.

Accordingly, it becomes possible to generate three-dimensional voxel data reflecting the calculated probabilities properly.

Moreover, the process may further include: (E) causing a brightness value of a voxel in the second three-dimensional voxel data to be approximated to a first brightness value representing that the voxel is inside the target object or a second brightness value representing that the voxel is outside the target object by finding out a solution of a reaction-diffusion equation for brightness values of voxels in the second three-dimensional voxel data.

Accordingly, it becomes possible to clarify the boundary between the target object and the portion that is not the target object even when the boundary is indistinct.

Moreover, the first generating may include: (a1) transforming a triangular-meshed reference shape of the target object so as to match the first region; and (a2) causing brightness values of an inside of the transformed reference shape to become the first brightness value and brightness values of an outside of the transformed reference shape to become the second brightness value to generate the first three-dimensional voxel data.

By using the reference shape as described here, three-dimensional voxel data generated at the end will become realistic.

Moreover, the first generating may include: (a3) specifying, from among voxels included in the first three-dimensional voxel data, voxels that correspond to a boundary between the target object and a portion that is not the target object; and (a4) applying a Gaussian filter to cause brightness values of the specified voxels to become an average of the first brightness value and the second brightness value.

It is reasonable that if a voxel value is the first brightness value or the second brightness value, an average of the first brightness value and the second brightness value corresponds to the boundary.

Moreover, the first generating may include: (a5) executing a processing based on a Region Growing method using, as a seed point, a voxel included in a portion that is not the target shape among voxels included in the first three-dimensional voxel data.

Accordingly, it becomes possible to separate the inside of the target shape from the outside because the portion that is not the target shape can be extracted.

Moreover, the target object may be a heart. By performing the aforementioned processings, a three-dimensional shape with high accuracy can be generated even when a complicated organ such as a heart is used.

Incidentally, it is possible to create a program causing a computer to execute the aforementioned processing, and such a program is stored in a computer readable storage medium or storage device such as a flexible disk, CD-ROM, DVD-ROM, magneto-optic disk, a semiconductor memory, and hard disk. In addition, the intermediate processing result is temporarily stored in a storage device such as a main memory or the like.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present inventions have been described in detail, it should be understood that the various changes, substitutions, and alterations could be made hereto without departing from the spirit and scope of the invention.

What is claimed is:

1. A non-transitory computer-readable storage medium storing a program for causing a computer to execute a process, the process comprising:
   first generating first three-dimensional voxel data that represents a target object by using first tomographic images, in which a first region occupied by the target object is designated, among a plurality of tomographic images;
   extracting, from the first tomographic images, brightness values of voxels included in the first region;
   second generating a function for calculating a probability that a voxel is included in the first region by using the extracted brightness values;
   calculating, for each voxel among voxels in a voxel space that includes the plurality of tomographic images, a probability by using a brightness value of the voxel and the function; and
   third generating second three-dimensional voxel data that represents the target object by using the first three-dimensional voxel data and probabilities calculated for the voxels in the voxel space.

2. The non-transitory computer-readable storage medium as set forth in claim 1, wherein the extracting comprises:
   second extracting brightness values of voxels included in a second region other than the first region, and
   the second generating comprises:
   fourth generating a first frequency distribution for the brightness values of the voxels included in the first region and a second frequency distribution for the brightness values of the voxels included in the second region;
   fifth generating the function for calculating the probability by dividing a value of the first frequency distribution by a sum of the value of the first frequency distribution and a value of the second frequency distribution for each brightness value in the first tomographic images.

3. The non-transitory computer-readable storage medium as set forth in claim 2, wherein the second extracting comprises:
   executing an erosion processing for the first region in the first tomographic images; and
   third extracting the brightness values from a region that is specified by the erosion processing and is other than the first region.

4. The non-transitory computer-readable storage medium as set forth in claim 1, wherein the third generating comprises:
   second calculating a value based on a brightness value of a first voxel included in the first three-dimensional voxel data and a probability calculated for a voxel that corresponds to the first voxel.

5. The non-transitory computer-readable storage medium as set forth in claim 1, wherein the process further comprises:
   causing a brightness value of a voxel in the second three-dimensional voxel data to be approximated to a first brightness value representing that the voxel is inside the target object or a second brightness value representing that the voxel is outside the target object by finding out a solution of a reaction-diffusion equation for brightness values of voxels in the second three-dimensional voxel data.

6. The non-transitory computer-readable storage medium as set forth in claim 5, wherein the first generating comprises:
   transforming a triangular-meshed reference shape of the target object so as to match the first region; and
   causing brightness values of an inside of the transformed reference shape to become the first brightness value and brightness values of an outside of the transformed reference shape to become the second brightness value to generate the first three-dimensional voxel data.

7. The non-transitory computer-readable storage medium as set forth in claim 6, wherein the first generating comprises:
specifying, from among voxels included in the first three-dimensional voxel data, voxels that correspond to a boundary between the target object and a portion that is not the target object; and
applying a Gaussian filter to cause brightness values of the specified voxels to become an average of the first brightness value and the second brightness value.

8. The non-transitory computer-readable storage medium as set forth in claim 6, wherein the first generating comprises:
executing a processing based on a Region Growing method using, as a seed point, a voxel included in a portion that is not the target shape among voxels included in the first three-dimensional voxel data.

9. The non-transitory computer-readable storage medium as set forth in claim 1, wherein the target object is a heart.

10. A shape data generation method, comprising:
first generating, by using a computer, first three-dimensional voxel data that represents a target object by using first tomographic images, in which a first region occupied by the target object is designated, among a plurality of tomographic images;
extracting, from the first tomographic images and by using the computer, brightness values of voxels included in the first region;
second generating, by using the computer, a function for calculating a probability that a voxel is included in the first region by using the extracted brightness values;
calculating, for each voxel among voxels in a voxel space that includes the plurality of tomographic images and by using the computer, a probability by using a brightness value of the voxel and the function; and
third generating, by using the computer, second three-dimensional voxel data that represents the target object by using the first three-dimensional voxel data and probabilities calculated for the voxels in the voxel space.

11. A shape data generation apparatus, comprising:
a memory; and
a processor configured to use the memory and execute a process, the process comprising:
first generating first three-dimensional voxel data that represents a target object by using first tomographic images, in which a first region occupied by the target object is designated, among a plurality of tomographic images;
extracting, from the first tomographic images, brightness values of voxels included in the first region;
second generating a function for calculating a probability that a voxel is included in the first region by using the extracted brightness values;
calculating, for each voxel among voxels in a voxel space that includes the plurality of tomographic images, a probability by using a brightness value of the voxel and the function; and
third generating second three-dimensional voxel data that represents the target object by using the first three-dimensional voxel data and probabilities calculated for the voxels in the voxel space.

\* \* \* \* \*